(12) United States Patent
Mueller et al.

(10) Patent No.: US 8,372,144 B2
(45) Date of Patent: Feb. 12, 2013

(54) IMPLANT WITH A BASE BODY OF A BIOCORRODIBLE IRON ALLOY

(75) Inventors: Heinz Mueller, Erlangen (DE); Joerg Loeffler, Schneisingen (CH); Peter Uggowitzer, Ottenbach (CH)

(73) Assignee: Biotronik VI Patent AG, Baar (CH)

( * ) Notice: Subject to any disclaimer, the term of this patent is extended or adjusted under 35 U.S.C. 154(b) by 360 days.

(21) Appl. No.: 12/366,247

(22) Filed: Feb. 5, 2009

(65) Prior Publication Data

US 2009/0198320 A1 Aug. 6, 2009

(30) Foreign Application Priority Data

Feb. 5, 2008 (DE) ............... 10 2008 007 746
Jun. 24, 2008 (DE) ............... 10 2008 002 601

(51) Int. Cl.
*A61F 2/06* (2006.01)
(52) U.S. Cl. .............. 623/1.38; 420/434
(58) Field of Classification Search .......... 623/1.15, 623/1.44, 1.46; 427/2.1, 2.25
See application file for complete search history.

(56) References Cited

U.S. PATENT DOCUMENTS

| | | | |
|---|---|---|---|
| 5,197,940 A | 3/1993 | Sievert et al. | |
| 6,287,332 B1 * | 9/2001 | Bolz et al. | 623/1.15 |
| 2005/0273156 A1 * | 12/2005 | Burgermeister et al. | 623/1.15 |
| 2006/0118758 A1 | 6/2006 | Wang et al. | |
| 2007/0191708 A1 * | 8/2007 | Gerold et al. | 600/431 |

FOREIGN PATENT DOCUMENTS

| | | |
|---|---|---|
| DE | 19731021 A1 | 1/1999 |
| DE | 69410555 T2 | 1/1999 |
| DE | 102004036954 A1 | 3/2006 |
| EP | 0 540 483 A1 | 5/1993 |
| EP | 0923389 A2 | 6/1999 |
| WO | 2007082147 A2 | 7/2007 |
| WO | 2007124230 A1 | 11/2007 |

OTHER PUBLICATIONS

Search Report for German Patent Application No. 10 2008 002 601.8; Oct. 29, 2008.
Hermawan et al.; Degradation Behaviour of Metallic Biomaterials for Degradable Stents; Advanced Materials Research; Thermec 2006 Supplement; pp. 113-118; vols. 15-17.
European Search Report issued in corresponding EP Application No. EP 08 17 2105 on Nov. 5, 2012.
Hermawan et al., "Degradation Behavior of Metallic Biomaterials for Degradable Stents," Advanced Materials Research vols. 15-17 (2007) pp. 113-118.

* cited by examiner

*Primary Examiner* — Thomas J Sweet
*Assistant Examiner* — Christopher D Prone
(74) *Attorney, Agent, or Firm* — Greer, Burns & Crain, Ltd.

(57) ABSTRACT

A base body for an implant comprising a biocorrodible iron alloy including at least one of the following: (i) a biocorrodible iron alloy of formula Fe—P where P is 0.01-5 wt %, and Fe plus impurities account for the remainder up to 100 wt %; or (ii) a biocorrodible iron alloy of formula Fe—Mn—X where Mn is 5-30 wt %, X is at least one of Pt, Pd, Ir, Rh, Re, Ru and Os, and X is 0-20 wt % and Fe plus impurities account for the remainder up to 100 wt %; or (iii) a biocorrodible iron alloy of formula Fe—Z where Z is at least one of Pt, Ir and Os and Z is 5-30 wt %, and Fe plus impurities account for the remainder up to 100 wt %.

19 Claims, 15 Drawing Sheets

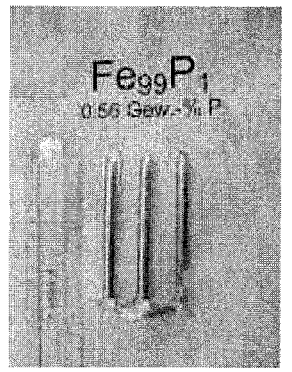 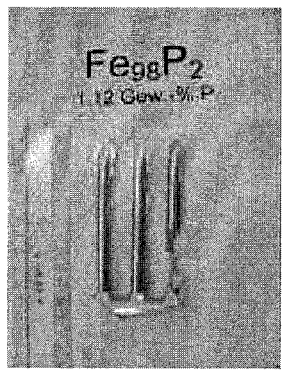 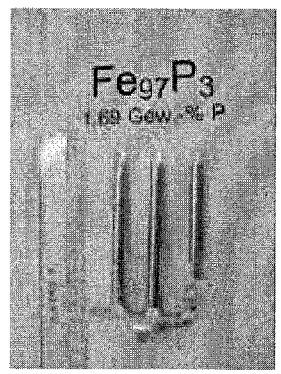
FIG. 2A   FIG. 2B   FIG. 2C
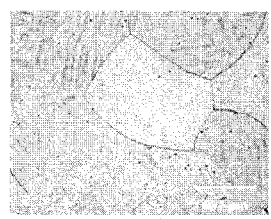 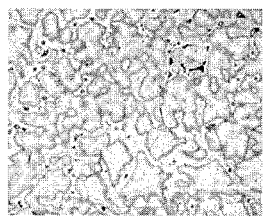 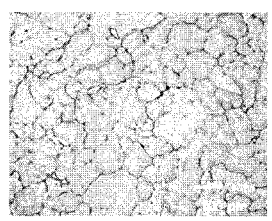 
FIG. 3A   FIG. 3B   FIG. 3C   FIG. 3D
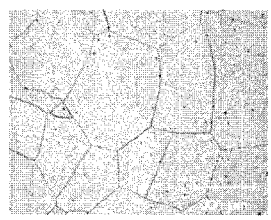 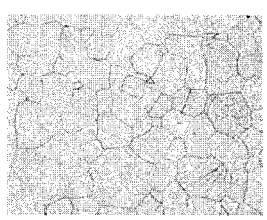 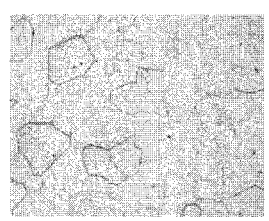 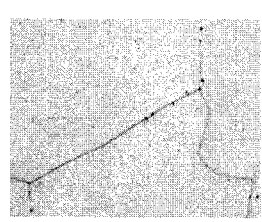
FIG. 4A   FIG. 4B   FIG. 4C   FIG. 4D

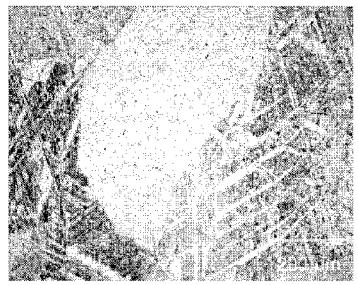 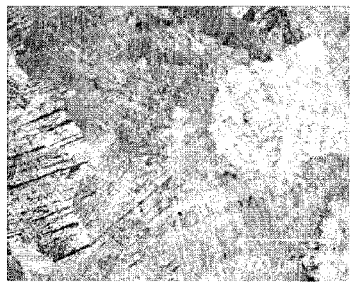 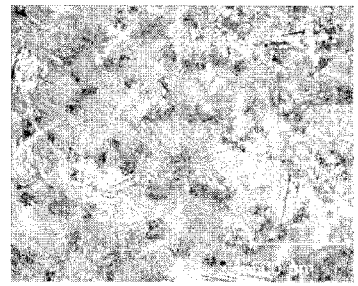
FIG. 12A     FIG. 12B     FIG. 12C
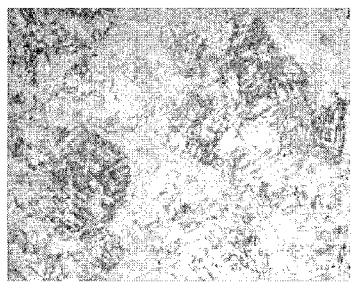  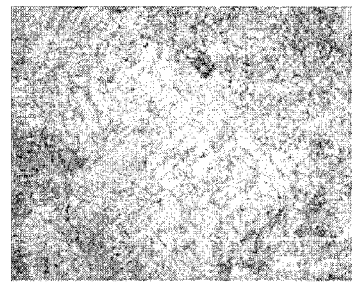
FIG. 13A     FIG. 13B     FIG. 13C
 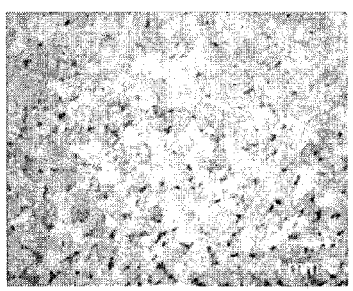 
FIG. 14A     FIG. 14B     FIG. 14C

IMPLANT WITH A BASE BODY OF A BIOCORRODIBLE IRON ALLOY

PRIORITY CLAIM

This patent application claims priority to German Patent Application No. 10 2008 007 746.1, filed Feb. 5, 2008, and German Patent Application No. 10 2008 002 601.8, filed Jun. 24, 2008, the disclosures of which are incorporated herein by reference in their entirety.

FIELD

The present disclosure relates to an implant with a base body consisting either entirely or partially of a biocorrodible iron alloy.

BACKGROUND

Implants are used in a variety of ways in modern medical technology. Implants serve, among other things, to support blood vessels, hollow organs and duct systems (endovascular implants), for fastening and temporary fixation of tissue implants and tissue transplants, and also for orthopedic purposes, e.g., as nails, plates or screws.

Implantation of stents is one of the most effective therapeutic measures in treatment of vascular diseases. Stents assume a supporting function in the hollow organs of a patient. Stents of a traditional design, therefore, have a filigree supporting structure of metallic struts, the structure initially being in a compressed form for introduction into the body and then dilated at the site of application. One of the main areas of application of such stents is for permanent or temporary dilation of vascular occlusions and maintaining vascular patency, in particular, for dilation of occlusions (stenoses) of the coronary vessels. In addition, aneurysm stents, which provide support for damaged vascular walls, are also known.

The base body of each implant, in particular, stents, comprises an implant material. For purposes of the present disclosure, an implant material is a nonviable material that is used for an application in medicine and interacts with biological systems. The basic prerequisites for use of a material as an implant material, which comes in contact with the biological environment when used as intended, is its biological compatibility (biocompatibility). For purposes of the present disclosure, biocompatibility is the ability of a material to induce an appropriate tissue reaction in a specific application. This includes an adaptation of the chemical, physical, biological and morphological surface properties of an implant to the recipient tissue with the goal of a clinically desired interaction. The biocompatibility of the implant material also depends on the chronological course of the reaction of the biosystem in which the implant is implanted. Thus, irritations and inflammations, which can lead to tissue changes, occur in the relatively short term. Biological systems thus react in different ways, depending on the properties of the implant material. According to the reaction of the biosystem, the implant materials can be subdivided into bioactive, bioinert and degradable/absorbable materials. For the purposes of the present disclosure only degradable/absorbable metallic implant materials are of interest. The degradable/absorbable metallic implant materials are referred to hereinbelow as biocorrodible metallic materials.

The use of biocorrodible metallic materials is recommended, in particular, because the implant often must remain in the body only a short period of time to fulfill the medical purpose. Implants of permanent materials, i.e., materials that are not degraded in the body, can optionally be removed again because there may be rejection reactions in the body in the medium range and in the long range even if there is a high biocompatibility.

One approach to avoid a further surgical intervention consists of making the implant either entirely or partially of a biocorrodible metallic material. For purposes of the present disclosure, "biocorrosion" refers to processes which are due to the presence of biological media and lead to a gradual degradation of the structure made of this material. At a certain point in time, the implant, or at least the part of the implant made of the biocorrodible material, loses its mechanical integrity. The degradation products are largely absorbed by the body. In the best case, the degradation products such as magnesium, for example, even have a positive therapeutic effect on the surrounding tissue. Small quantities of unabsorbable alloy constituents are tolerable, as long as they are nontoxic.

Known biocorrodible metallic materials comprise pure iron and biocorrodible alloys of the main elements magnesium, iron, zinc, molybdenum and tungsten. Among other things, it is proposed in German Patent Application No. 197 31 021 that medical implants should be made of a metallic material having as its main component an element from the group consisting of alkali metals, alkaline earth metals, iron, zinc and aluminum. Alloys based on magnesium, iron and zinc are described as being especially suitable. Secondary constituents of the alloys may include manganese, cobalt, nickel, chromium, copper, cadmium, lead, tin, thorium, zirconium, silver, gold, palladium, platinum, silicon, calcium, lithium, aluminum, zinc and iron. Regardless of advances made in the field of biocorrodible metal alloys, the alloys known so far can be used only to a very limited extent because of their corrosion behavior. In particular, the relatively slow biocorrosion of pure iron or the known iron alloys limits their possible applications.

Traditional fields of use of molded bodies of metallic materials, in particular, iron alloys outside of medical technology usually require extensive suppression of corrosion processes. Accordingly, the purpose of most technical methods for improving the corrosion behavior is to completely inhibit corrosion processes. However, the purpose of improving the corrosion behavior of the biocorrodible iron alloys in the present disclosure is not to completely suppress corrosion processes but rather to accelerate the corrosion processes. Furthermore, toxicological aspects must also be taken into account for any application in medical technology. Finally, corrosion processes depend greatly on the medium in which the corrosion processes take place. Therefore, it is usually impossible to transfer findings about the properties of specific iron alloys obtained in the technical field under traditional nonphysiological environmental conditions to the processes in a physiological environment.

International Patent Publication No. WO 2007/082147 relates to bioerodable endoprostheses having at least two sections of metallic materials with different corrosion rates. Iron alloys with the following compositions are mentioned as examples: (i) 88 to 99.8 wt % Fe, 0.1-7 wt % Cr, 0-3.5 wt % Ni and less than 5 wt % other elements and (ii) 90 to 96 wt % Fe, 3-6 wt % Cr, 0-3 wt % Ni and 0-5 wt % other metals. When using the elements Cr and Ni in a biocorrodible material, a substantial negative effect on biocompatibility must be expected. Chromium, in particular, is among the elements having a very high toxicity potential.

Hendra Hermawan et al. describe the degradation behavior of a stent made of the Fe-35Mn alloy (*Advanced Materials Research*, vols. 15-17, (2007), pp. 113-116). However, this alloy has only a marginally increased corrosion. Another disadvantage is that the relatively high Mn content in a monophase structure suggests a reduced ductility.

Another disadvantage of an alloy with 35 wt % Mn is that after cooling, transformation to so-called $\epsilon$-(epsilon)-martensite is no longer possible.

Another disadvantage of an alloy with 35% Mn is that a two-phase structure cannot be achieved here. However, a fine-grained two-phase structure is the basis of extremely good plasticity. One disadvantage of the loss of this multiphase property is that the austenite stability can no longer be adjusted with carbon or nitrogen.

Biocorrodible alloys of iron and carbon are also known (for example, in European Patent Application No. 0 923 389 and International Patent Publication No. WO 2007/124230). One disadvantage of these alloys is that a pure binary system of iron and carbon shows a great decline in ductility with an increase in carbon content without a comparable decline in corrosion resistance.

One feature of the present invention provides a biocorrodible iron alloy having improved corrosion behavior for an implant. This should take place, in particular, in such a way that the additional material properties that are important for processing, e.g., ductility, are not impaired.

SUMMARY

The present disclosure describes several exemplary embodiments of the present invention.

One aspect of the present disclosure provides an implant having a base body, the base body at least partially comprising at least one of the following: (i) a biocorrodible iron alloy of formula (1) Fe—P, where the amount of P in the alloy is from 0.01 to 5 wt %, and Fe plus impurities due to the production process account for the remainder of the alloy up to 100 wt %; or (ii) a biocorrodible iron alloy of formula (2) Fe—Mn—X, where the Mn content of the alloy is from 5 to 30 wt %, X is one or more elements selected from the group Pt, Pd, Ir, Rh, Re, Ru and Os, and the amount of X in the alloy is from 0 to 20 wt %, and Fe plus impurities due to the production process account for the remainder of the alloy up to 100 wt %; or (iii) a biocorrodible iron alloy of formula (3) Fe—Z, where Z is one or more elements selected from the group Pt, Ir and Os, and the amount of Z in the alloy is from 5 to 30 wt %, and Fe plus impurities due to the production process account for the remainder of the alloy up to 100 wt %.

Another aspect of the present disclosure provides a method for production of an implant, comprising a. providing a biocorrodible iron alloy comprising at least one of the following: (i) Fe—P (1), where the amount of P in the alloy is 0.01 to 5 wt % and Fe plus impurities due to the production process account for the remainder of the alloy up to 100 wt %; or (ii) Fe—Mn—X (2), where the amount of Mn in the alloy is 5 to 30 wt %, X is one or more elements selected from the group of Pt, Pd, Ir, Rh, Re, Ru and Os, and the amount of X in the alloy is 0 to 20 wt % and Fe plus the impurities due to the production process account for the remainder of the alloy up to 100 wt %; or (iii) Fe—Z (3), where Z is one or more elements selected from the group Pt, Ir and Os, and the amount of Z in the alloy is 5 to 30 wt % and Fe plus impurities due to the production process account for the remainder of the alloy to 100 wt %; and b. forming an implant from the biocorrodible iron alloy.

A further aspect of the present disclosure provides a method production of an implant designed for temporary fixation of tissue, comprising: a. providing a biocorrodible iron alloy comprising at least one of the following: (i) Fe—P (1), where the amount of P in the alloy is from 0.01 to 5 wt % and Fe plus impurities due to the production process account for the remainder of the alloy up to 100 wt %; or (ii) Fe—Mn—X (2), where the amount of Mn in the alloy is from 5 to 30 wt %, X is one or more elements selected from the group of Pt, Pd, Ir, Rh, Re, Ru and Os, and the amount of X in the alloy is from 0 to 20 wt %, and Fe plus impurities due to the production process account for the remainder of the alloy up to 100 wt %; or (iii) a Fe—Z (3), where Z is one or more elements selected from the group Pt, Ir and Os, and the amount of Z in the alloy is from 5 to 30 wt %, and Fe plus impurities due to the production process account for the remainder of the alloy up to 100 wt %; and, b. forming an implant from the biocorrodible iron alloy.

With the help of the inventive implant, one or more of the disadvantages of the state of the art described hereinabove can be overcome or at least ameliorated.

It has been found that iron alloys of formulas Fe—P, Fe—Mn—X and Fe—Z have a definitely increased susceptibility to corrosion in comparison with pure iron in an artificial medium simulating physiological conditions.

In addition, it has surprisingly been found that two-phase regions occur in the structures of the iron alloys of formulas Fe—Mn—X and Fe—Z to an increasing extent. These are paramagnetic to some extent, so that the magnetic properties of the metallic material change considerably in comparison with those of pure iron, for example. Associated with this, interactions of the metallic material with magnetic fields are reduced, which reduces the formation of artifacts in MRI scans, in particular.

The compositions of the iron alloys are to be selected such that the compositions will be biocorrodible. For purposes of the present disclosure, biocorrodible alloys are alloys in which a degradation/conversion takes place in a physiological environment so that the part of the implant made of the material is either no longer present at all or is at least not predominantly present. As the test medium for testing the corrosion behavior of an alloy in question, a synthetic plasma such as that specified according to EN ISO 10993-15:2000 for biocorrosion tests is used (composition NaCl 6.8 g/L, CaCl$_2$ 0.2 g/L, KCl 0.4 g/L, MgSO$_4$ 0.1 g/L, NaHCO$_3$ 2.2 g/L, Na$_2$HPO$_4$ 0.126 g/L, NaH$_2$PO$_4$ 0.026 g/L). A sample of the alloy to be tested is stored in a sealed sample container with a defined amount of the test medium at 37° C. At intervals of a few hours up to several months, depending on the corrosion behavior to be expected, the samples are removed and examined for traces of corrosion in a way known in the art. The artificial plasma according to EN ISO 10993-15:2000 corresponds to a medium resembling blood and thus simulates a physiological environment.

In the Fe—P system, corrosion resistance is reduced continuously by additional alloying of phosphorus. In experiments, corrosion resistance has been reduced by a factor of up to 3 in comparison with pure iron by additional alloying of up to 3 at % phosphorus in artificial plasma (simulated body fluid, hereinafter "SBF"). With an increase in P content, there is an increase in strength and a decline in plasticity.

| SBF | [mmol/L] |
|---|---|
| Na$^+$ | 142.0 |
| K$^+$ | 5.0 |
| Mg$^{2+}$ | 1.0 |
| Ca$^{2+}$ | 2.5 |
| Cl$^-$ | 109.0 |

-continued

| SBF | [mmol/L] |
|---|---|
| $HCO_3^-$ | 27.0 |
| $HPO_4^{2-}$ | 1.0 |
| $SO_4^{2-}$ | 1.0 |
| pH | 7.3-7.4 |

If manganese (Mn) is alloyed to pure iron according to formula Fe—Mn—X, the corrosion resistance can also be reduced. In experiments, a substantial reduction in corrosion resistance has been measured, in particular, with additional alloying of 10 or 20 wt % Mn. The weight loss of a sample stored in SBF amounted to 3.5× to 6× in comparison with that of pure iron. The amount of Mn in the iron alloy of formula Fe—Mn—X is therefore preferably 10 to 27 wt %.

The development of the structure in these alloy systems has an unusual feature. Unalloyed iron has a body-centered cubic ("bcc") alpha-lattice (also known as α-iron or ferrite) which is ferromagnetic and is, therefore, also responsible for the strong artifacts in imaging by MRI methods. With an increase in manganese content, the development of this bcc phase is increasingly suppressed. This occurs because, with a sufficiently high manganese content in the alloy, two phases may exist in thermodynamic equilibrium: the bcc phase described herein and a face-centered cubic ("fcc") phase, the so-called γ-phase (also known as austenite). This fcc phase is paramagnetic and thus does not cause the artifacts described hereinabove or does so only to a very minor extent. The development of the structure here is such that not all the structural components (grains) form the bcc phase, but instead, with an increase in Mn content, more grains increasingly have the face-centered cubic structure. Such a structure having two phases in equilibrium is known as a duplex structure.

Above an Mn content in the range of 30 wt %, the structure becomes completely austenitic. It should be noted here that depending on the cooling rate in the production of the alloy, transformation of the fcc phase into the bcc phase and/or into a corresponding duplex structure can be suppressed even at an Mn content of significantly less than 30%, and then a purely austenitic structure is obtained. The development of the duplex structure described hereinabove has various effects. First, with an increase in fcc content, the interaction with magnetic fields is reduced, and specifically, the artifacts produced in MRI scans are reduced. Another effect of the two phases being present concurrently is that the existence of phases that are both more noble and less noble electrochemically has the effect of accelerating corrosion. Furthermore, this two-phase structure can be produced in a very fine-grained form and can be very stable with respect to grain growth, i.e., even after thermomechanical treatments, they remain fine-grained and therefore are also ductile. Thus, good plasticity and good ductility are also to be expected despite an increase in hardness with an increase in Mn content.

Due to the fact that two phases develop with these materials, given a suitable adjustment of the alloy contents, one of which is a ferromagnetic phase and the other a paramagnetic phase, while at the same time one phase is electrochemically more noble and the other phase is less noble, therefore, the electrochemical behavior, specifically the degradation rate in a physiological environment as well as the magnetic behavior of the material can be adjusted through the alloy composition, i.e., the manganese content and optionally also other alloy elements that are present. This property may thus be used to produce biodegradable materials having a controllable degradation rate.

It should be pointed out that manganese is essential for all biological organisms. However, there are no known deficiency phenomena in humans, even high overdoses being tolerated well. The daily requirement is 0.4-10 mg. In animal experiments, manganese has been identified as an essential element for formation of bone and cartilage. Other animal experiments have shown deficiencies in insulin production along with changes in lipoprotein metabolism and disturbances in the metabolism of growth factors in manganese-deficient animals. Manganese may also be an essential cofactor for the conversion of preprothrombin to prothrombin. Biochemical studies have also shown that manganese is a cofactor for a number of enzymes, including arginase and alkaline phosphatase of the liver and for pyruvate carboxylase. Manganese also increases the activity of succinate dehydrogenase and prolidase as well as a few enzymes of mucopolysaccharide synthesis. Accordingly, release of small quantities of manganese in the body as a result of degradation of the alloy is toxicologically unobjectionable.

By additional alloying of one or more of the aforementioned alloy elements X (Pt, Pd, Ir, Rh, Re, Ru, Os), the corrosion resistance of iron-manganese alloys can be further reduced. This has been proven on the Fe—Mn—Pd system, for example, where the corrosion rate, measured by the weight loss of a sample stored in SBF, can be increased by a factor of more than 30 by additional alloying of 0.2 to 5% palladium into alloys containing 10% or 20% Mn. All the properties described above with regard to the possible adjustment of phase components in the structure, the magnetic properties and/or the corrosion behavior are preserved with these ternary or multi-alloy systems. Preferably, in particular, in combination with the exemplary alloy embodiments mentioned hereinabove with an Mn content of 10 to 20 wt %, the amount of X in the iron alloy of formula Fe—Mn—X is 0.01 to 10 wt %. X especially preferably is Pd.

If development of a ferromagnetic phase is not desirable in such a biodegradable alloy system based on Fe and Mn, there is the possibility of achieving this with carbon and nitrogen as additives to the alloy. Fe—Mn alloys behave so that a completely face-centered cubic structure can be obtained in the presence of carbon with a much lower Mn content. The same effect can also be achieved with additional alloying of nitrogen. This method is known from the production of the nickel-free austenitic steels. Here again, the concentration of manganese which is necessary for complete austenitazation is lowered. Alloying of nitrogen or carbon into the Fe—Mn system thus opens a possibility of, first of all, optimizing the degradation properties with regard to an accelerated degradation and at the same time optimizing the structure with regard to the best possible plasticity or with regard to its MR compatibility. A combination of these exemplary alloy embodiments with the exemplary alloy embodiments described hereinabove having an Mn content of 10 to 20 wt % and/or an X content of 0.01 to 10 wt % is especially preferred.

In the iron alloy of formula Fe—Z, Z is one or more elements selected from the group consisting of Pt, Ir and Os and the amount of Z in the alloy is 5 to 30 wt %. The elements iridium and platinum, in particular, behave fundamentally like manganese with regard to the development of phases. Here again, duplex structures can be created with a suitable temperature program. Due to the very positive standard potentials of platinum and iridium, two phases with different electrochemical properties develop. The degradation process is accelerated by formation of elements locally between the two phases.

For purposes of the present disclosure, implants are devices introduced into the body by a surgical method or a minimally invasive method, including fastening elements for bones, e.g., screws, plates or nails, surgical suture material, intestinal clamps, vascular clips, prostheses in the area of the heart and soft tissue, e.g., stents and anchoring elements for electrodes, in particular, pacemakers or defibrillators. The implant is made either entirely or in part of the biocorrodible material.

The implant is preferably a stent. Stents of a traditional design have a filigree structure of metallic struts that are initially in an unexpanded state for introduction into the body and then are dilated to an expanded state at the site of application.

The implant is especially preferably designed as an implant for treatment of hyperthermia, i.e., the implant is created for these purposes. In particular, the implant is used and/or adapted accordingly for tumor therapy by radiofrequency ablation. The implant is, therefore, of a type such that it is heated by induction in an alternating magnetic field. The implant is designed so that it is suitable for the purposes of treating hyperthermia, including the stipulation of a geometry adapted to the site of administration and an interaction with the pathogen.

This is where another special property of alloy systems such as Fe—Mn, Fe—Pd, Fe—Ir, Fe—Pt, is manifested in particular. These iron alloys open the so-called γ-field, i.e., the temperature at which the α+γ-duplex structure having a ferromagnetic and a paramagnetic content is converted into the paramagnetic γ-structure and is shifted continuously downward with an increase in the alloy content. The α–γ-transformation temperature of pure iron may thus be lowered, e.g., to levels below 100° C. in some cases through the alloy technology, e.g., depending on the choice of the system. This, in turn, means that the ferromagnetic phase, which has a significant influence on the heating because of its much greater interaction with magnetic fields, disappears above a certain temperature and thus further heating of such a component or implant fails to occur until the temperature has dropped to the extent that the ferromagnetic α-phase can develop again. As a result, this means that the temperature never rises above a limit value. This limit value can be controlled by adjusting the phase amounts of the structure. For example, if large amounts of the aforementioned alloy elements are additionally alloyed, then the resulting structure has a low temperature at which the structure becomes completely paramagnetic and, even in the coexistence range of the two phases, only a very small amount of the structure is in the ferromagnetic γ-phase. For example, such a material can only be heated to comparatively low temperatures and furthermore is clearly below the transformation temperature because of the constant dissipation of heat in the resulting temperature. This can be used to limit the temperatures, e.g., in an RF ablation process, and therefore to avoid excessive tissue damage due to excessively high temperatures when used as a biodegradable alloy for the production of implants for hyperthermia treatment. In an alternating magnetic field, the implants for hyperthermia treatment made of the iron alloy as disclosed in the present application thus experience a defined heating. This offers for the first time the possibility of using biodegradable implants with a definable degradation kinetics for treatment of hyperthermia, e.g., as part of a tumor therapy.

Another aspect of the present disclosure is the use of a biocorrodible iron alloy of formulas Fe—Mn—X and Fe—Z for the production of an implant designed for treatment of hyperthermia.

In addition to the possibility of heating in an alternating electromagnetic field, at least partially ferromagnetic iron alloys of formulas Fe—P, Fe—Mn—X and Fe—Z, i.e., those with a sufficiently broad hysteresis curve have a permanent magnetic moment after an alignment of the magnetic moments. This property can be utilized to manufacture implants that can be used to secure tissue against tissue by utilizing magnetic attractive forces as long as the implants are degraded. Another aspect of the present disclosure is the use of a biocorrodible iron alloy of formulas Fe—P, Fe—Mn—X and Fe—Z for the production of an implant designed for temporary fixation of tissue.

Another particular feature of the alloys is manifested in plastic deformation. If alloys of the group Fe—Mn—X, e.g., Fe—Mn—Pd, undergo plastic deformation, two particular properties can be observed.

First, the so-called consolidation of these alloys is extremely high, i.e., the alloys can undergo plastic deformation with relatively low stresses (forces). During the deformation, the strength of the alloy increases continuously and greatly. The ratio of yield point (onset of plastic deformation) and maximum strength is unusually high here. For example, in preliminary experiments with the FeMn15Pd1 alloy, a yield point in the range of 350 MPa and a maximum strength (ultimate tensile strength) in the range of 900 MPa were found. The strength of these alloys is thus considerably greater than that of surgical stainless steel (316L) and almost achieves the strength levels of CoCr alloys, such as L605 or MP35N, the alloys with the highest strength that are used for stents.

In addition, another particular feature in deformation of these alloys consists of the fact that a strain-induced phase transition occurs in deformation. This means that at least a portion of one phase is converted to the second phase of the duplex structure in the two-phase structure. In the present disclosure, this occurs in such a way that the amount of the ferromagnetic phase increases in the deformation.

If these alloys are used for implants that are to undergo plastic deformation, such as balloon-expandable stents, in particular, then the great consolidation in plastic deformation has various advantages.

Due to the great increase in strength of the material, stents achieve a high radial strength. At a given radial strength, the thickness of the profiles of the structure, the so-called struts, can also be designed to be essentially filigree. This filigree design of struts has already led to significantly improved clinical results in the past when using CoCr alloys. Since the strength of the new alloys described here has already almost reached the level of the CoCr alloys, it is possible to expect comparable strut thicknesses and advantages for the implant.

Minimization of strut thicknesses also leads to the result that, in the case of a degradable implant, less material must be introduced into the body which reduces the risk of bio-incompatible reactions while at the same time leading to a shortened degradation period.

Finally, an additional effect is a reduction in the overall profile of the stent delivery system ("SDS") with the stent installed.

The property whereby the ferromagnetic content of the structure increases when there is plastic deformation of such alloys can be utilized at the moment when the implant is to be heated in an alternating electromagnetic field, as described hereinabove. In this case, the interaction with the field is greater and an equally strong effect can be achieved with a smaller volume of material.

The implant of the biocorrodible iron alloy is, in particular, a stent for blood vessels, the bile duct, urethra, esophagus, and the like, i.e., a supporting or connecting implant for all vessels, duct systems or anastomoses in the human body.

In addition, the implant of the biocorrodible iron alloy is, in particular, a clip for closing off severed blood vessels. For example, a V-shaped clip with which a severed blood vessel is closed by pinching together the clip using forceps at the end of the vessel, i.e., is plastically deformed so that it closes the end of the vessel, stopping the blood flow and resulting in thrombosis.

Furthermore, the implant of the biocorrodible iron alloy may, in particular, be an implant that is used to reliably reclose vessels into which a cannula or catheter having a large diameter has been inserted temporarily, after removing the temporary implant, in order to prevent bleeding at this location. In this case, the implant is typically in the form of a clamp which is implanted by means of an application system with which claws or tips extend around the location of the vascular wall to be closed and press the opening closed.

Finally, the implant of the biocorrodible iron alloy is, in particular, an occluder. An occluder is a fixation system that can be administered in a minimally invasively procedure with which a septum defect (PFO), for example, can be secured until the cardiac septum has grown together and the defect has closed naturally. Then the implant can be degraded biologically. For example, the implant here is designed so that a long tubular structure is compressed by means of a tensile force upstream and downstream from the defect and is plastically deformed so that a screen form develops on both sides of the defect, pressing the two parts of the open cardiac septum together.

BRIEF DESCRIPTION OF THE DRAWINGS

Various aspects of the present disclosure are described hereinbelow with reference to the accompanying figures.

FIGS. 2A-C are test specimens after casting in a vacuum induction furnace;
FIGS. 3A-D are structures of the test specimens in the cast state;
FIGS. 4A-D are structures of the test specimens in the homogenized state;
FIGS. 12A-C are micrographs for the alloys Fe-20Mn-xPd;
FIGS. 13A-C are micrographs for the alloys Fe-10Mn-xPd after solution annealing;
FIGS. 14A-C are micrographs of the alloys Fe-20Mn-xPd after solution annealing.

DETAILED DESCRIPTION

Fe—P System

Production of the Alloy

Figure 1A:
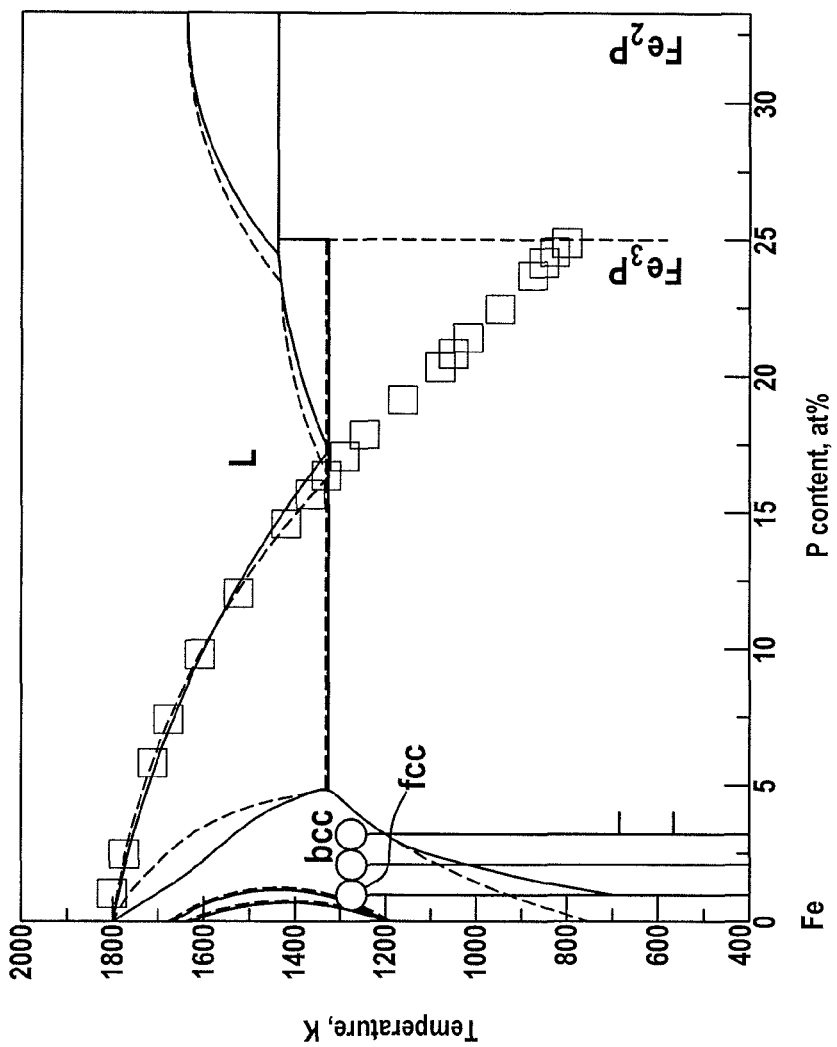
FIG. 1A is a diagram of an Fe—P phase.
Figure 1B:
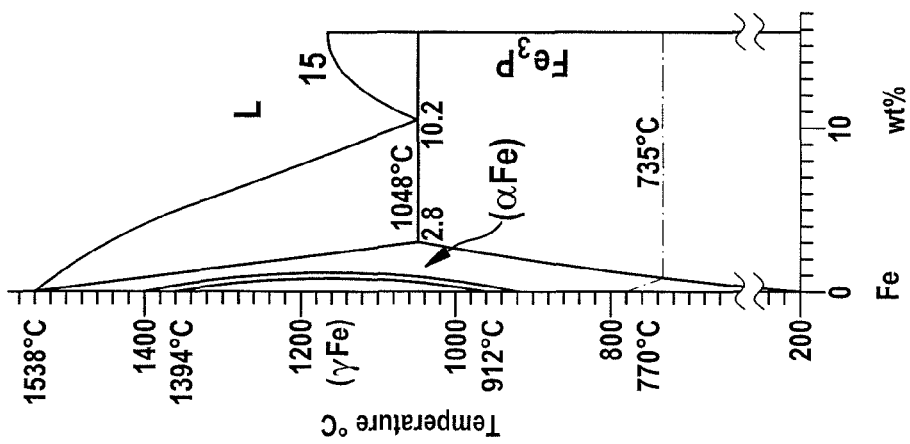
FIG. 1B is the Fe-rich section of the Fe—P phase diagram of FIG. 1A.

FIG. 1B shows the Fe-rich section of an Fe—P phase diagram (FIG. 1A). For the purposes of the present disclosure, the following important features can be derived from this phase diagram:
1) P greatly restricts γ-region, so P is a strong ferrite stabilizer;
2) a low-melting eutectic ($T_e$=1048° C.) is formed with iron phosphide $Fe_3P$;
3) the maximum solubility is only 2.8 wt %, corresponding to 4.9 at %.

In smelting the specimen, the following points were taken into account accordingly:
1) The composition should be inside the single-phase ferrite range so that a highly embrittling $Fe_3P$ eutectic is not formed if the material later undergoes plastic deformation;
2) In smelting, the alloy is in imbalance so homogenizing annealing should be performed. Consequently, the composition should not be too close to the maximum solubility because otherwise the temperature window for the annealing treatment becomes too narrow;
3) To be able to study the influence of P on structure as well as mechanical and electrochemical properties, an alloy series with at least three P levels should be smelted.

An alloy series with 1 at %, 2 at % and 3 at % corresponding to 0.56 wt %, 1.12 wt % and 1.69 wt % was selected (see right partial figure in FIG. 1).

Smelting of the alloys was performed in a vacuum induction furnace with a batch weight of approximately 400 g. Phosphorus in the form of an iron phosphide prealloy was additionally alloyed. The specimen was cast in a vacuum induction furnace using a multipart Cu chill mold which made it possible to cast rods as specimens (FIG. 2).

Metallographic Characterization

FIG. 3 shows structures of the test specimens in the cast state, i.e., FIG. 3a: $Fe_{99}P_1$, FIG. 3b: $Fe_{98}P_2$, FIG. 3c: $Fe_{97}P_3$, FIG. 3d: $Fe_{97}P_3$, detail enlarged by a factor of 4. The marked segregation tendency is apparent. Whereas the structure of the alloy with 1 at % P is present in a single phase in the coarse grain, alloys with 2 and 3 at % P already have eutectic contents because of the imbalance in solidification. These structure ranges have an extremely embrittling effect. For example, it was possible to "manually" break the incompletely filled sample rods on the right at the thin places as shown in FIG. 2, namely with the typical fracture pattern of an intercrystalline brittle fracture.

To convert the test alloys into a near-equilibrium state, solution annealing was performed at 1000° C. (1270K) (see points of state in FIG. 1A, right). According to the phase diagram, single-phase ferritic structures should be achievable. FIG. 4 shows the structure of the alloys investigated after annealing for 2 hours and then quenching in water.

FIG. 4 shows the structures of the test specimens in the homogenized state (100° C./2 h/water); FIG. 4a: $Fe_{99}P_1$, FIG. 4b: $Fe_{98}P_2$, FIG. 4c: $Fe_{97}P_3$, FIG. 4d: $Fe_{97}P_3$ detail enlarged by a factor of 7. The single-phase state can be seen here. The eutectic phase components have broken up completely.

Hardness measurements on the polished specimens show the significant hardening effect due to phosphorus as an alloy element. The hardness increases from HV10=95±15 in pure iron to HV10=160±10 in Fe$_{99}$P$_1$, HV10=230±10 in Fe$_{98}$P$_2$ and HV10=290±10 in Fe$_{97}$P$_3$. This pronounced solid solution hardening effect is associated with embrittlement.

The P content in the iron alloy of formula Fe—P is preferably 0.01 to 1.2 wt %.

Figure 5A:
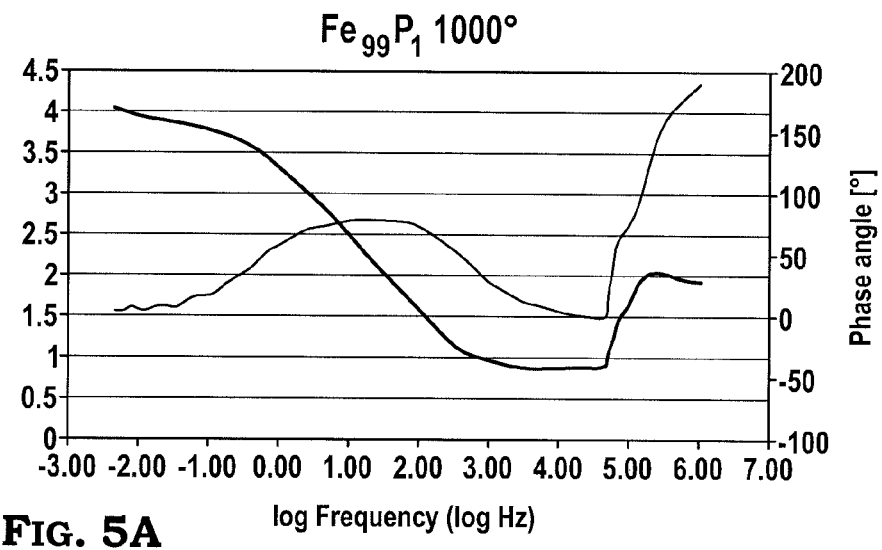
FIGS. 5A-C are Bode plots of the alloys tested.
Figure 5B:
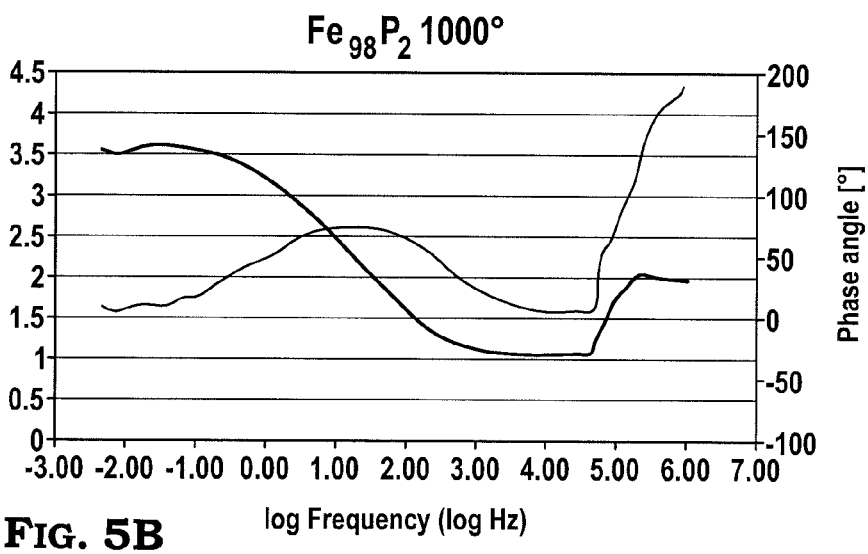
Figure 5C:
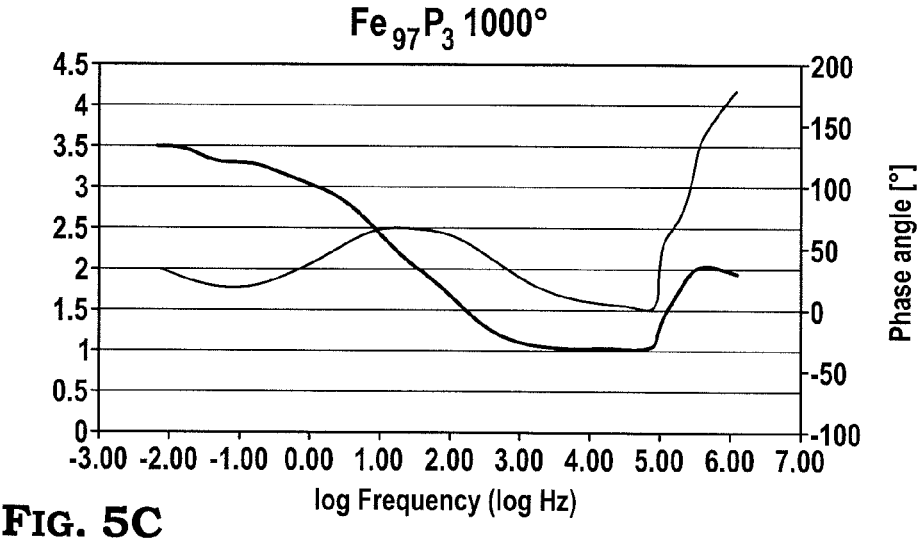

Corrosion Behavior—Electrochemical Impedance Spectroscopy (EIS) and Degradation Experiments The electrochemical properties of pure iron and/or the alloys were determined with the help of impedance spectroscopy under the following conditions: test temperature: 22.9° C.; test medium: SBF, pH 8.14; reference electrode: Hg—Hg—Cl; counter-electrode: platinum; test area Ø 7.4 mm. The Bode plots are shown in FIG. 5.

The EIS results show that the susceptibility to corrosion increases due to the alloying of phosphorus. An estimate with the values of the impedance at low frequencies yields at a value lower by a factor of approximately 3 for alloys with 1 and 2 at % P.

Fe—Mn System
Production of Alloy

Test specimens of the following compositions were smelted on a laboratory scale:
pure iron (Fe);
pure iron+10 wt % manganese (Fe-10Mn); and
pure iron+20 wt % manganese (Fe-20Mn).

These specimens were produced in an electric arc furnace under an argon atmosphere. The batch weight was approximately 7 g. Accordingly, the alloy product was an ellipsoidal test specimen with a diameter of approximately 10 to 12 mm.

Metallographic Characterization

Figure 6:
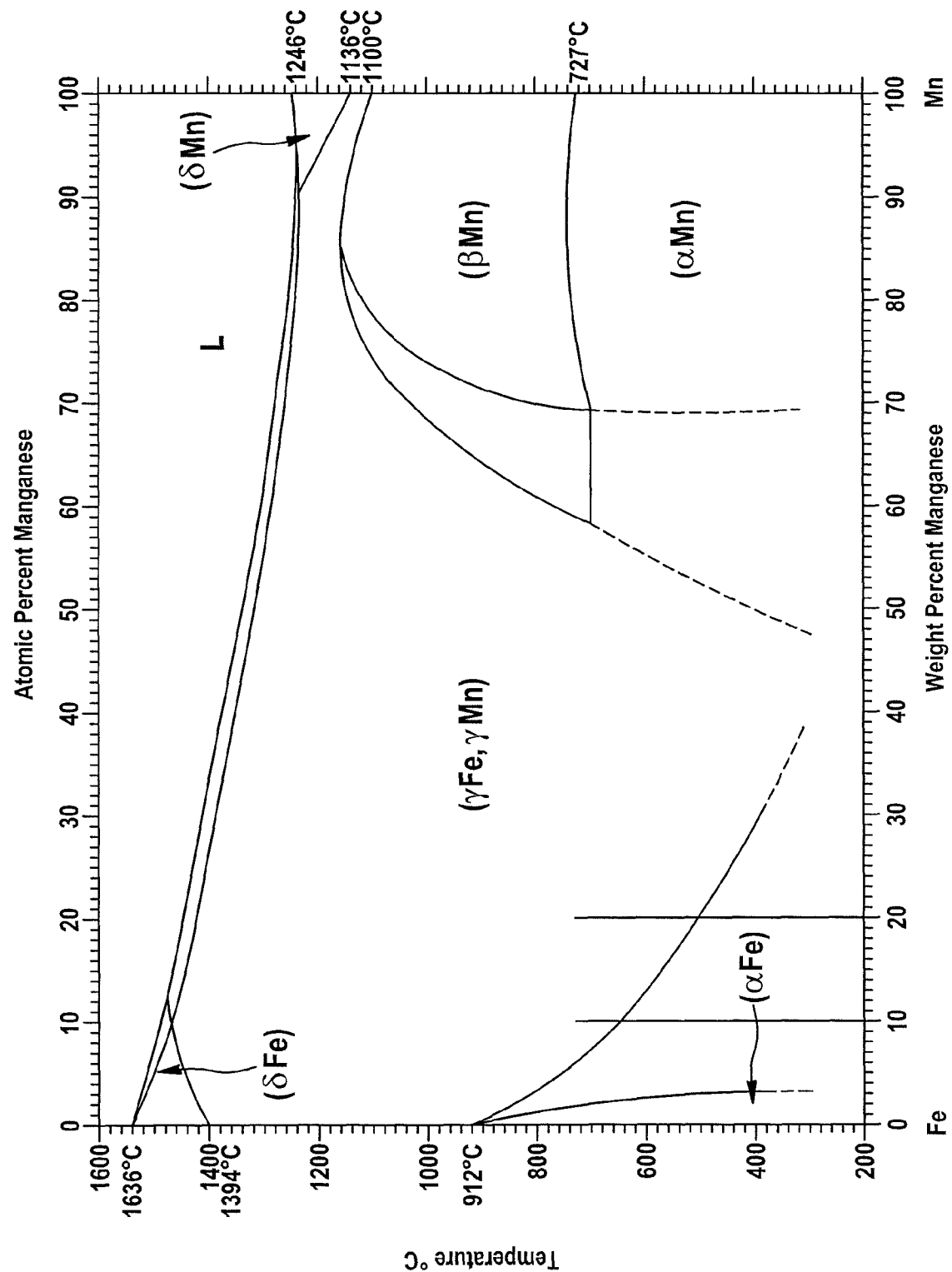
FIG. 6 is a phase diagram for Fe—Mn.
Figure 7C:
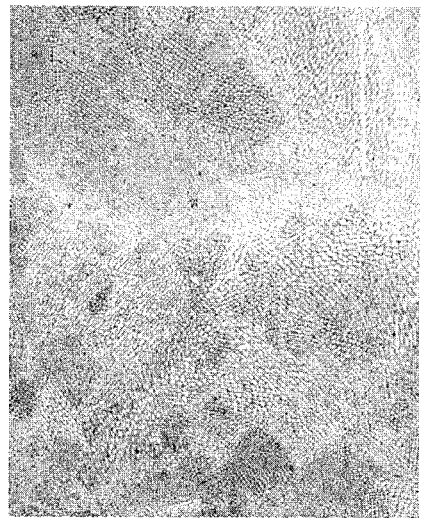
FIGS. 7A-C are micrographs of the alloys.
Figure 7B:
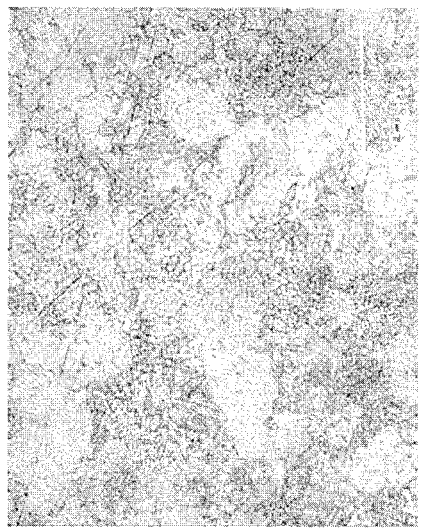
Figure 7A:
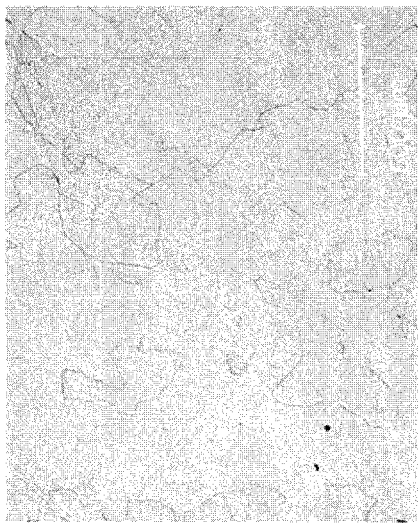

FIG. 6 shows the binary Fe—Mn system with characteristic lines for the selected compositions. For alloys with between 10 and 20 wt % manganese, a two-phase α+γ structure is to be expected. The micrographs in FIG. 7 confirm this assumption; these are micrographs of the alloys Fe (left), Fe-10 Mn (center) and Fe-20Mn (right). The two phases α-Fe and γ-Fe can be discerned. However, it should be pointed out that these cast structures are not yet completely in equilibrium. However, recrystallized structures with smaller grain size can be created by homogenizing annealing with subsequent shaping.

Hardness measurements on the polished specimens show the significant hardening effect due to manganese as an alloy element. The hardness increases from HV10=95±15 in pure iron to HV10=220±10 in Fe-10Mn and HV10=230±10 in Fe-20Mn. Because of the face-centered cubic γ-phase, an increase in ductility is also to be expected in the alloys with 10% and 20% Mn.

Corrosion Behavior—Electrochemical Impedance Spectroscopy (EIS)

Figure 8A:
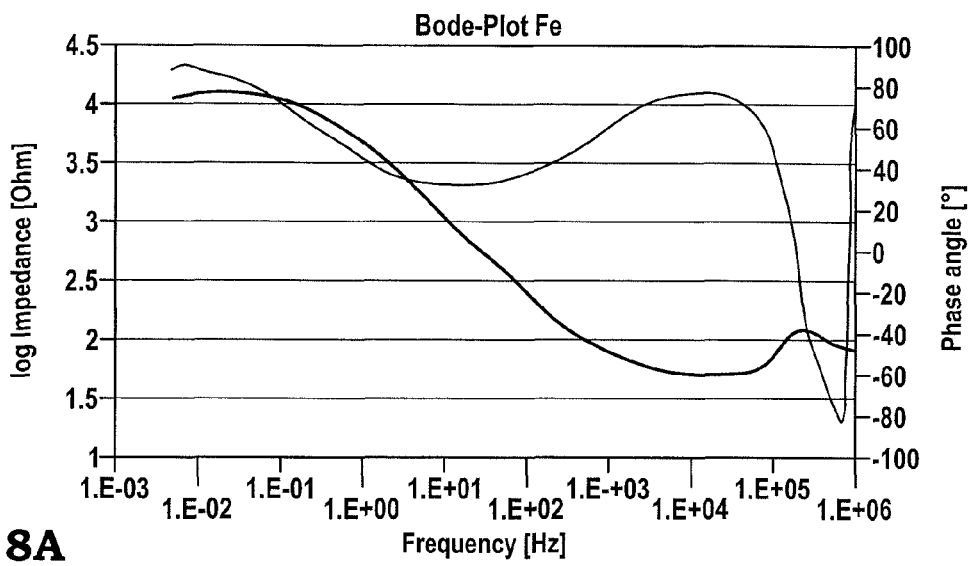
FIGS. 8A-C are Bode plots of the alloys tested.
Figure 8B:
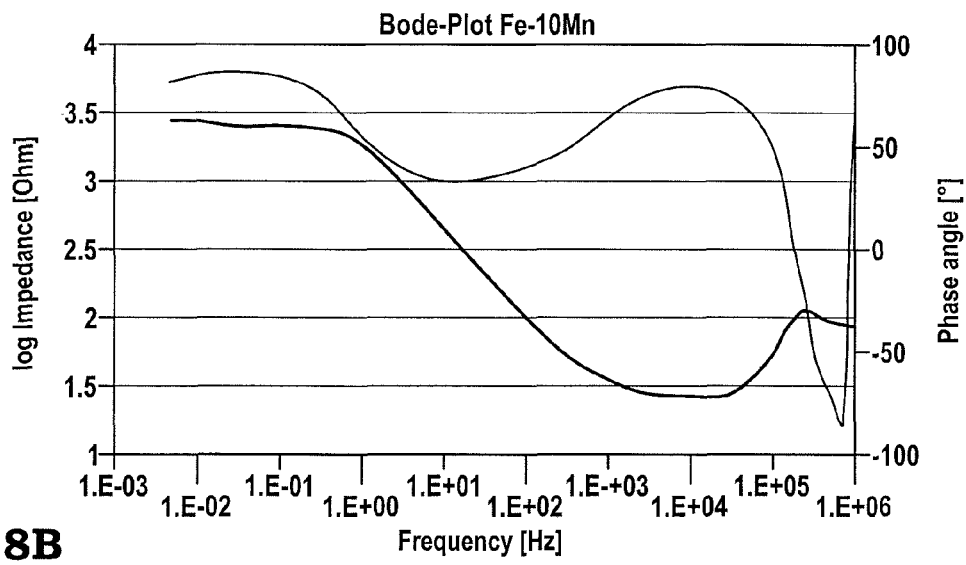
Figure 8C:
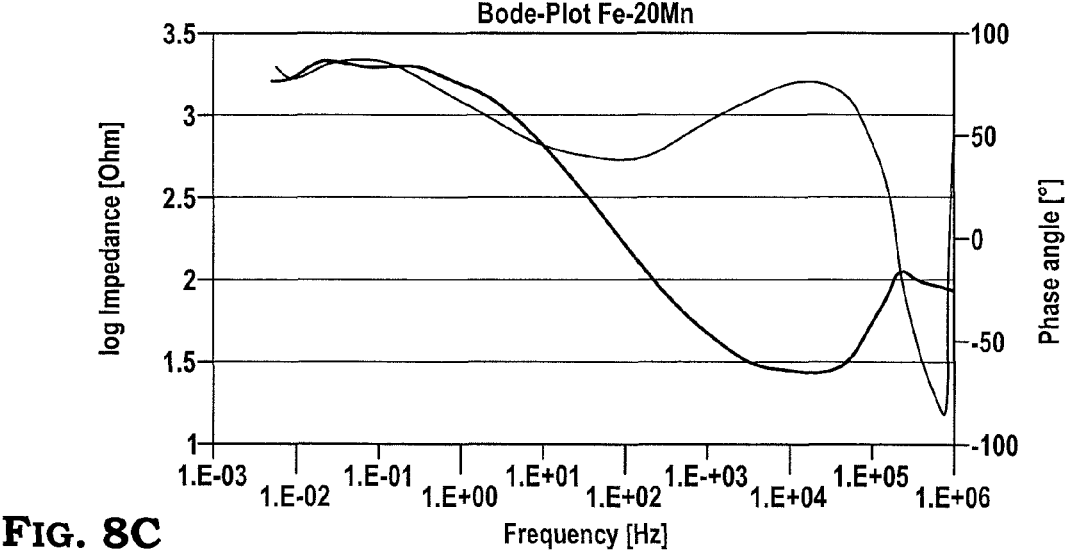

The electrochemical properties of pure iron and the alloys were determined with the help of impedance spectroscopy under the following conditions: specimen temperature, 22.9° C.; test medium, SBF, pH 8.14; reference electrode, Hg—Hg—Cl; counter-electrode, platinum; test area Ø 7.4 mm. The Bode plots are shown in FIG. 8.

The EIS results show that the susceptibility to corrosion increases significantly due to the additional alloying of manganese. An estimate using the impedance values at low frequencies yields a lower value for the alloy with 10% manganese by a factor of 3.5 but the value for the alloy with 20% manganese is lower by a factor of approximately 6.

Fe—Mn—X System

By additional alloying of "noble" elements X, finely distributed "noble" precipitates are formed which act as cathodic sites and thus lead to increased galvanic corrosion. Various aspects should be taken into account in the selection of the elements X: i) the elements should have a limited solubility, i.e., should form precipitates; ii) the resulting second phases, usually intermetallic phases (IMP), should have the highest possible noble metal content so that they also have a strongly cathodic effect; and, iii) biocompatibility should be ensured.

The binary system of the elements Fe and Pd makes Pd appear especially suitable. All the possible IMPs contain at least 50 at % Pd whereas, in the case of Pt, IMPs with a lower Pt content are also formed. In the case of Ir and Rh, the binary systems with Mn have not been documented well enough to allow comparable statements.

As can be deduced from the Fe—Mn system, the γ–α-transformation is associated with substantial changes in concentration. Since the transformation is shifted toward lower temperatures with an increase in the Mn content, diffusion is greatly impeded. Above an Mn content of 5 wt %, austenite is not converted to ferrite at the usual cooling rate with an equalization of concentration, but instead there is a diffusionless shear-type transformation to cubic martensite.

Figure 9:
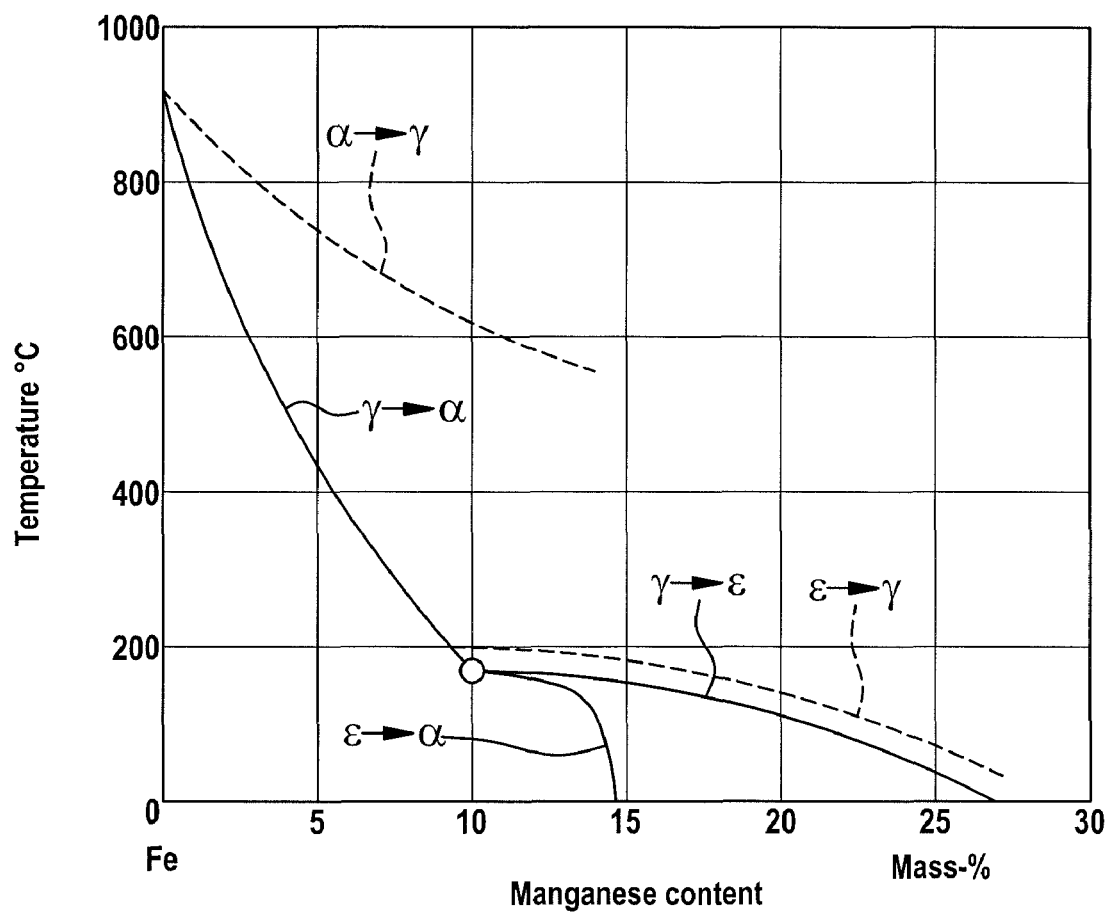
FIG. 9 is a real phase diagram for Fe—Mn.

FIG. 9 shows the real diagram of Fe—Mn alloys. The transformation to martensite extends over a larger temperature interval. With a subsequent heating, the reverse transformation begins as soon as the α→γ line, which is at much higher temperatures, is reached. This phenomenon, known as irreversibility, occurs with Fe—Mn alloys up to approximately 10%. Between 10% and 14.5% Mn, hexagonal ε-martensite is initially formed during cooling and is then converted to α-martensite. On reheating, the α-martensite is already transformed back to austenite between 200° C. and 300° C. but α-martensite is transformed only at much higher temperatures. In alloys with <14.5% Mn, only the γ→ε-transformation takes place during cooling, but it is incomplete and there are always large quantities of residual austenite. On reheating, the reverse transformation takes place at only slightly higher temperatures. The γ→ε-transformation can be suppressed completely by rapid cooling. The transformation behavior may thus be interpreted as meaning that there is always an austenitic structure at a temperature of >600° C. in alloys with >10% Mn. Because of the significantly lower diffusion in austenite in comparison with ferrite and martensite, "fine" segregation of Pd-containing IMPs can be expected in a corresponding annealing treatment.

Production of the Alloy

The following alloys were produced:
pure iron;
Fe-10 wt % Mn, each with 0%, 0.2%, 1% and 5 wt % Pd; and
Fe-20 wt % Mn, each with 0%, 0.2%, 1% and 5 wt % Pd.

The starting materials were:
iron powder: Ø<200 μm, purity>99%
manganese powder: Ø<200 μm, purity>99.9%
palladium, purity>99.99%

In each case, 50 to 60 g alloy was produced. To do so, a starting mixture was rapidly melted in an Al$_2$O$_3$ crucible in a vacuum induction furnace at 0.3 bar argon and cast in the form of studs (diameter approximately 10.5 mm). The studs were then cut into disks approximately 3 mm thick.

Heat Treatments

For the heat treatments, the cleaned sample disks were welded in quartz glass tubes at 0.3 bar argon. The treatments were performed in the pretreated annealing furnace and the specimens were quenched in water immediately on coming from the furnace (unless otherwise mentioned). The quartz glass tubes were crushed in water so the specimens were quenched in direct contact with the water. The following heat treatments were performed:
- 2 h at 1100° C.
- 2 h at 1100° C., 1 h at 700° C.
- 10 h at 1100° C.
- 10 h at 1100° C., 5 h at 700° C.
- 10 h at 1100° C., 5 h at 600° C.
- 10 h at 1100° C. and slow cooling (100° C./h) to room temperature
- 10 h at 1100° C. and slow cooling (100° C./h) to room temperature, 5 h at 700° C.
- 10 h at 1100° C. and slow cooling (100° C./h) to room temperature, 5 h at 600° C.

Examinations Under a Light Microscope

The ground and polished specimens were examined under a light microscope. To visualize the structure, the following etchants were used:
- Fe m3 for alloys with 20% manganese: 100 mL Klemm stock solution+2 g potassium disulfite; Klemm stock solution: 300 mL distilled water (40° C.)+1000 g sodium thiosulfate
- For Fe and Fe-10% Mn exemplary embodiments, Nital was used as the etchant.

Impedance Measurements

The impedance measurement allows an assessment of the corrosion behavior: a low impedance (at low measurement frequencies) indicates a low corrosion resistance. The measurements were performed with an impedance spectrometer of the AUTOLAB PGSTAT302 type.

Test medium: SBF. Reference electrode: Hg—Hg—Cl. Counter-electrode: platinum. Test area of specimens: 72 mm$^2$.

The edge of the specimens embedded in Bakelite was sealed with silicone before the measurement to prevent crevice corrosion between the specimen and the Bakelite.

Degradation Experiments

Two different exemplary embodiments of the experiments were used. For the first exemplary embodiment, holes were drilled in the specimen disks (Ø 3 mm), which were attached to a polymer thread and immersed in SBF. For the second exemplary embodiment, the specimens were attached with the help of small polymer holders and immersed in SBF in this way, using covered 3-liter glass beakers as containers. The SBF was circulated by a magnetic stirrer during degradation. The progress of degradation was determined by the weight loss of the specimens. To do so, the specimens were removed from the SBF, then cleaned first in distilled water and next in ethanol with ultrasound and dried under compressed air.

Microstructure

Figure 10A:
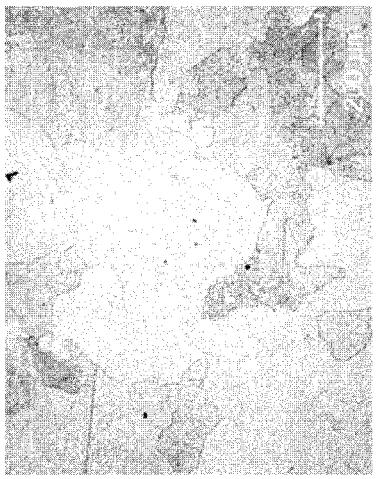
FIGS. 10A-C are micrographs of pure iron.
Figure 10B:
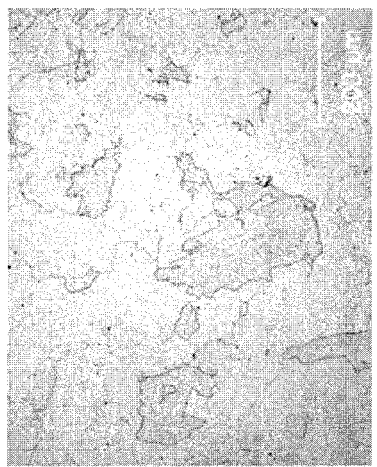
Figure 10C:

FIG. 10 shows micrographs of pure iron (left: 1100°/2 h; center: 1100°/10 h; right: 1100°/2 h+700° C./1 h). A ferritic structure is discernible.

Figure 11A:
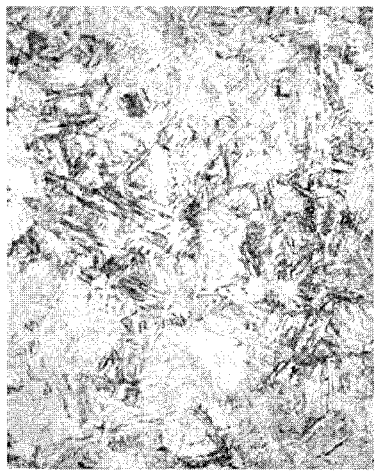
FIGS. 11A-C are micrographs for the alloys Fe-10Mn-xPd.
Figure 11B:
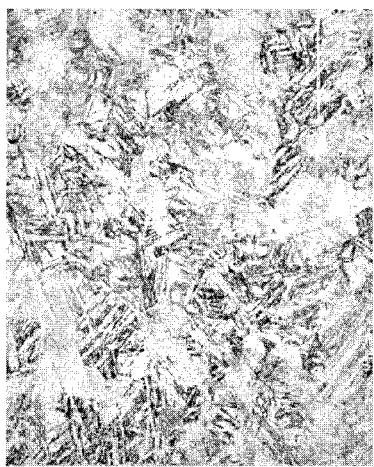
Figure 11C:
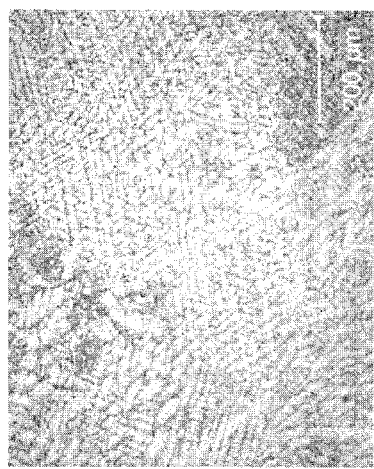

FIG. 11 shows micrographs of the alloys Fe-10Mn-xPd (1100° C./2 h; left: x=0; center: x=1.0; right: x=5). This is an α-martensite and a great segregation of Pd is discernible at 5% Pd.

FIG. 12 shows micrographs of the alloys Fe-20Mn-xPd (1100° C./2h; left: x=0; center: x=1.0; right: x=5). This shows an ε-martensite and there is a marked segregation of Pd at 1% and 5% Pd.

FIG. 13 shows micrographs of the alloys Fe-10Mn-xPd (1100° C./10 h+700° C./1 h; left: x=0; center: x=1.0; right: x=5). This shows an α-martensite, and segregation of Pd is discernible at 5% Pd.

FIG. 14 shows micrographs of the alloys Fe-20Mn-xPd (1100° C./10 h+700° C./1 h; left: x=0; center: x=1.0; right: x=5). This shows austenite and ε-martensite, and segregation of Pd is discernible at 5% Pd.

The diagrams in FIGS. 10 through 12 illustrate, as an example, the structure achieved as a function of the composition in the condition after 2 hours of solution annealing and quenching. The great tendency to segregation is noteworthy. An attempt was made to compensate for this by longer solution annealing. The illustrations in FIGS. 13 and 14 show the structure after these longer solution annealing treatments. A wrought alloy treatment may be performed to compensate for the segregation. The difference in etching behavior, which is indicative of different chemical properties, is also noteworthy.

It should be pointed out that after storage at 600° C. and/or 700° C., no development of segregation was discernible under the light microscope. It can be concluded from this that segregations much smaller than 1 µm in size have been formed.

Hardness Measurement

Figure 15:
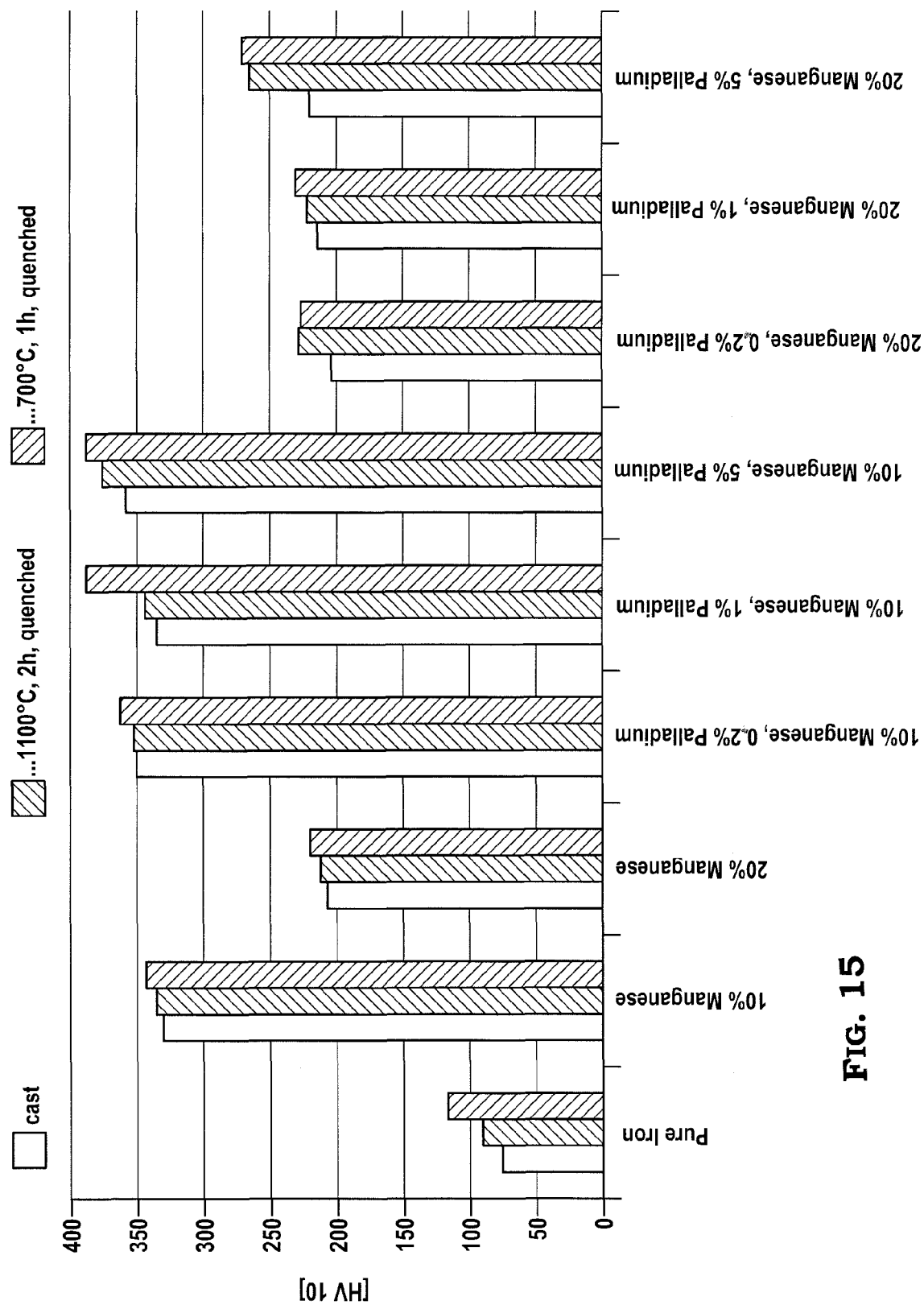
FIG. 15 is a graph of hardness values of the alloys in the state 1100° C./2 h+700° C./1 h.

FIG. 15 shows hardness values for the alloys in the condition after 1100° C./2 h+700° C./1 h. As assumed, it is found that mainly the manganese content and/or the resulting structure are crucial for the hardness. The ferritic structure (pure iron) is the softest, followed by the austenitic structure (20% manganese) and the martensitic structure (10% manganese).

Ferrite and Martensite Content

Table 1 shows the measured values for the ferrite/martensite content. The data are consistent with the results of the micrographs and the hardness measurements. The structure is determined largely by the manganese content. Pure iron is ferritic (always values of approximately 100% ferrite), alloys with 20% manganese are austenitic (always values of <4% ferrite and/or "no measurement" because they are pure austenite). However, the great differences in the measured values of the alloys with 10% manganese are noteworthy. They may increase or decrease significantly due to the various heat treatments, which corresponds to an increase and/or decrease in the austenite content.

TABLE 1

Ferrite/martensite content in percent

| | 1100° C., 2 h, quenched | | 1100° C., 10 h, quenched | |
| --- | --- | --- | --- | --- |
| | — | +700° C., 1 h, quenched | +600° C., 5 h, quenched | +700° C., 5 h, quenched |
| pure iron | 97.9 | 100 | 100 | 100 |
| 10% Mn | 75.8 | 81.9 | — | — |
| 20% Mn | 0.16 | <1 | 3.3 | 3.6 |
| 10% Mn, 0.2% Pd | 84.7 | 60.9 | 78.3 | 85.3 | 85.6 |
| 10% Mn, 1% Pd | 86.8 | 63.4 | 86.7 | 83.5 | 83.1 |
| 10% Mn, 5% Pd | 82.4 | 76.8 | 90.3 | 77.5 | 79.1 |
| 20% Mn, 0.2% Pd | 0.25 | <1 | <1 | <1 | <1 |
| 20% Mn, 1% Pd | n.m. | <1 | <1 | <1 | <1 |
| 20% Mn, 5% Pd | n.m. | <1 | 2.9 | 0.48 | 0.6 |

Corrosion Behavior—Electrochemical Impedance Spectroscopy (EIS)

Figure 16A:
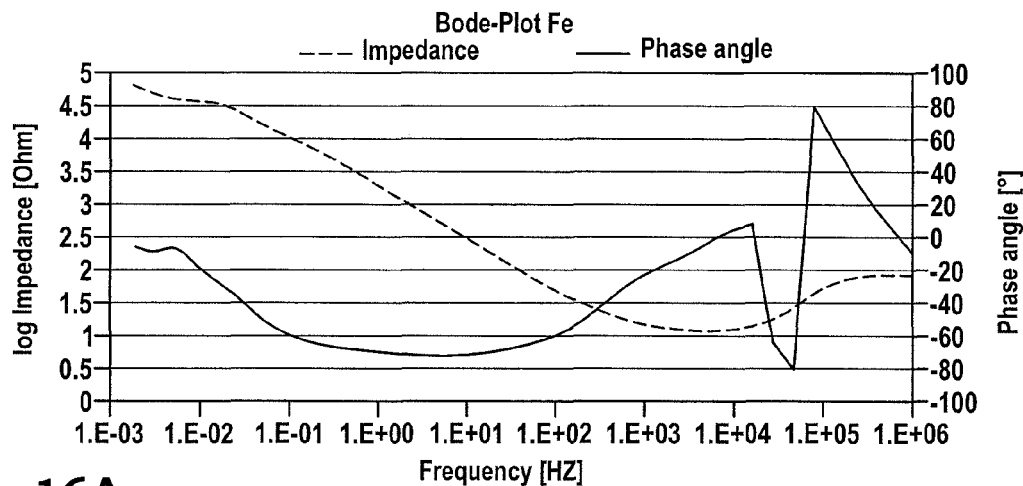
FIGS. 16A-C are Bode plots of the Pd-free alloys tested (1100° C./2 h++700° C./1 h)
Figure 16B:
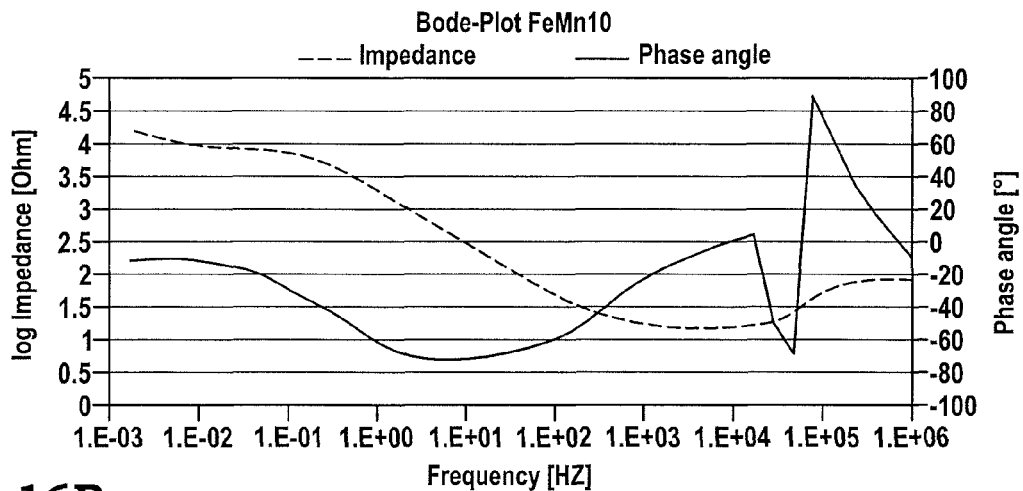
Figure 16C:
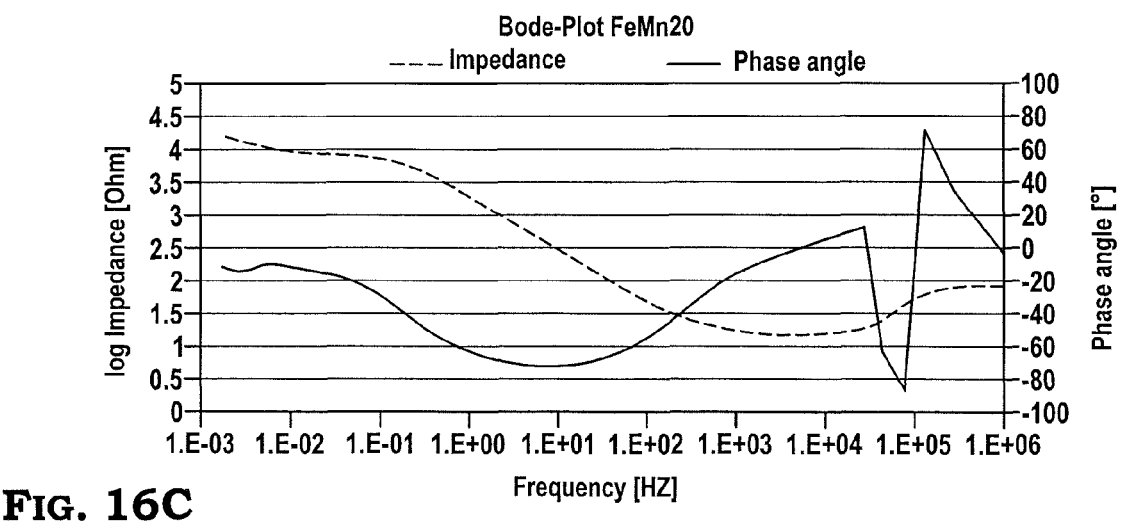
Figure 17A:
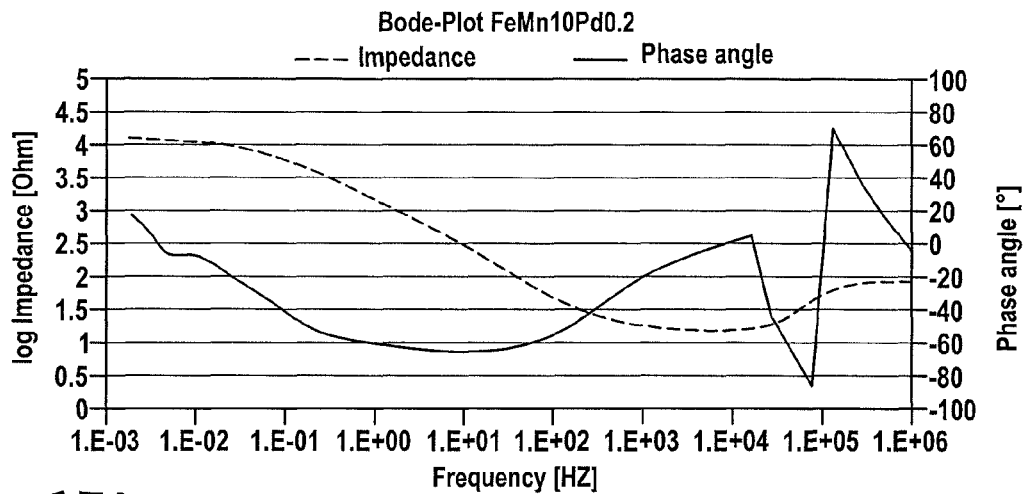
FIGS. 17A-C are Bode plots of the alloys tested with 10% Mn (1100° C./2 h+700° C./1 h)
Figure 17B:
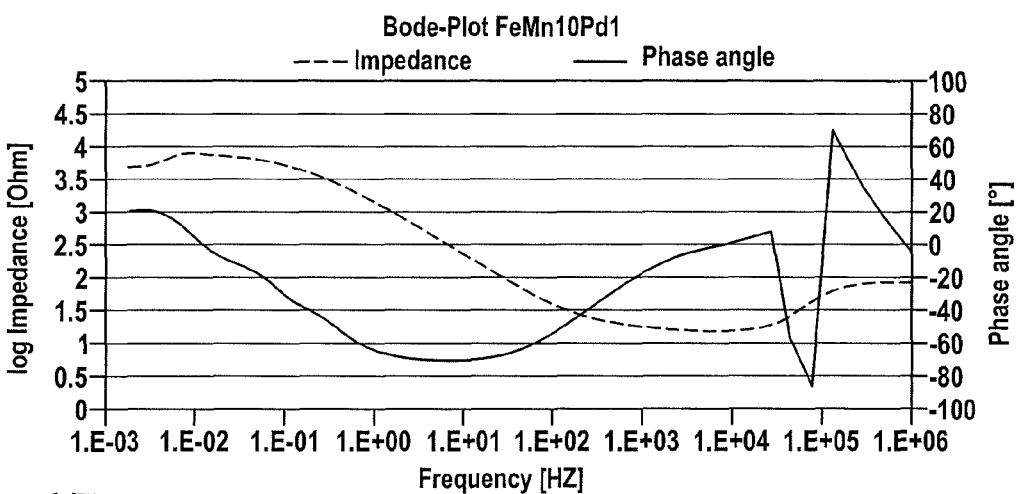
Figure 17C:
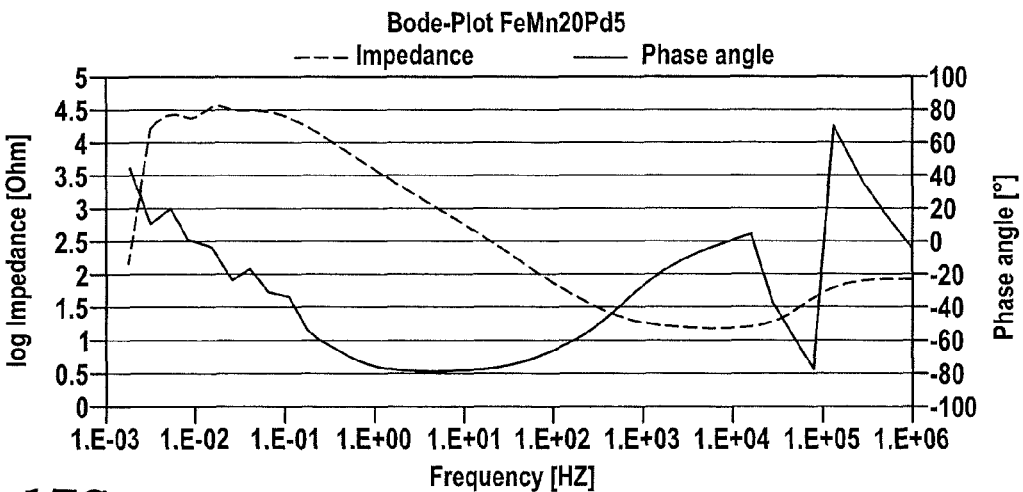
Figure 18A:
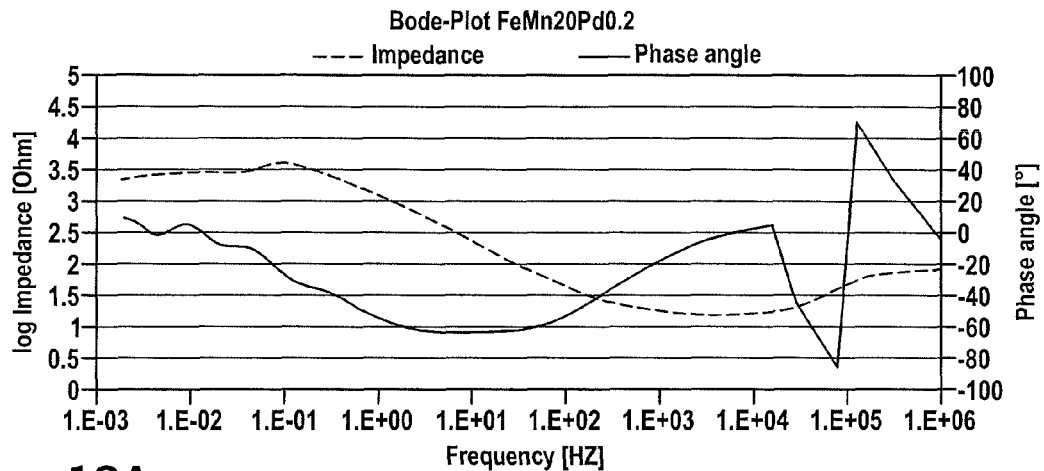
FIGS. 18A-C are Bode plots of the alloys tested with 20% Mn (1100° C./2 h+700° C./1 h)
Figure 18B:
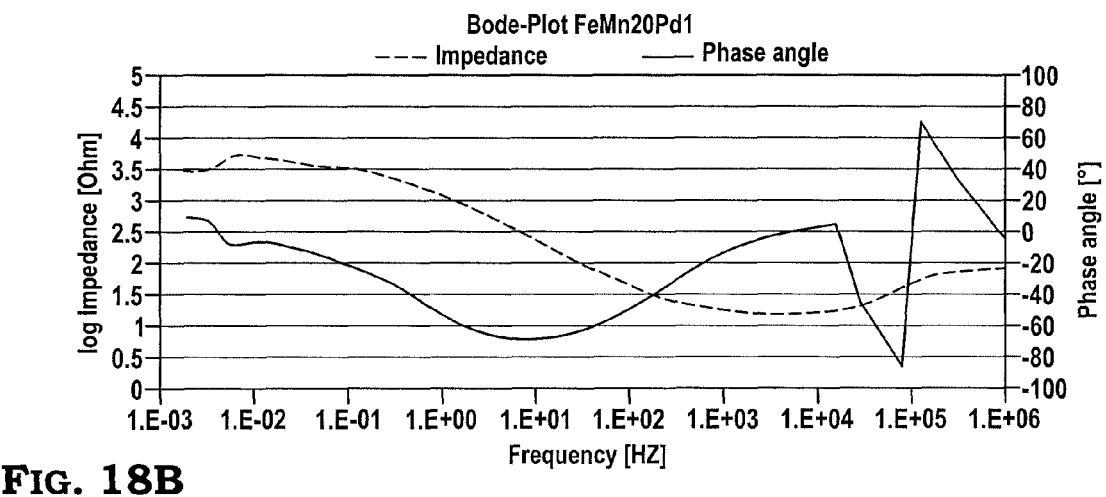
Figure 18C:
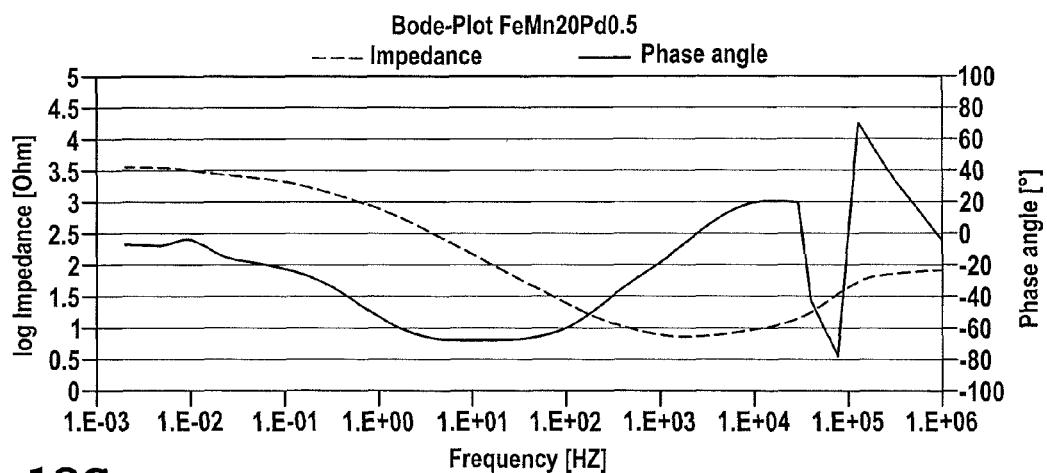

FIG. 16 shows Bode plots of the Pd-free alloys tested (1100° C./2 h+700° C./1 h). FIG. 17 shows Bode plots of the alloys tested with 10% Mn (1100° C./2 h+700° C./1 h). FIG. 18 shows Bode plots of the alloys with 20% Mn tested (1100° C./2 h+700° C./1 h).

The EIS results show that the susceptibility to corrosion obviously increases significantly due to additional alloying of manganese and Pd. At 20% manganese and 5% palladium, for example, the lowest value is found, which is smaller than that of pure iron by a factor of more than 10. It may thus be assumed that Mn and Pd have a corrosion-promoting effect. This is also confirmed by degradation experiments in SBF as described in the next section.

Degradation Experiments in SBF

Figure 19:
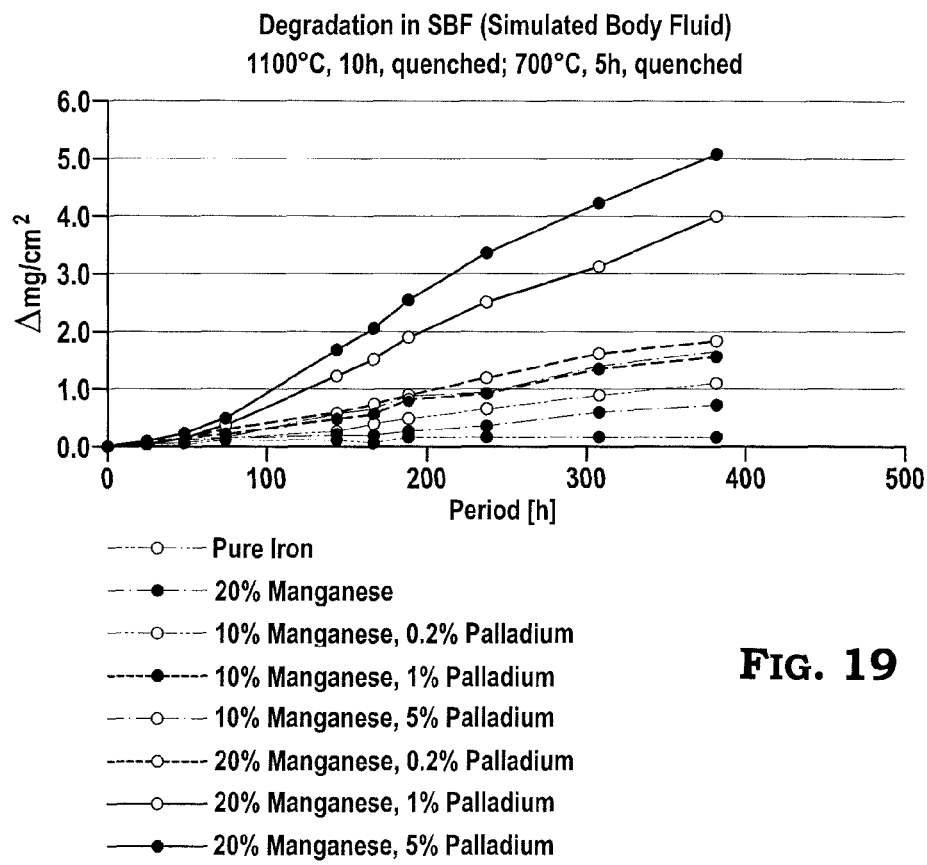
FIG. 19 is a graph of weight loss in SBF (1100° C./10 h/$H_2O$+700° C./5 h)
Figure 20:
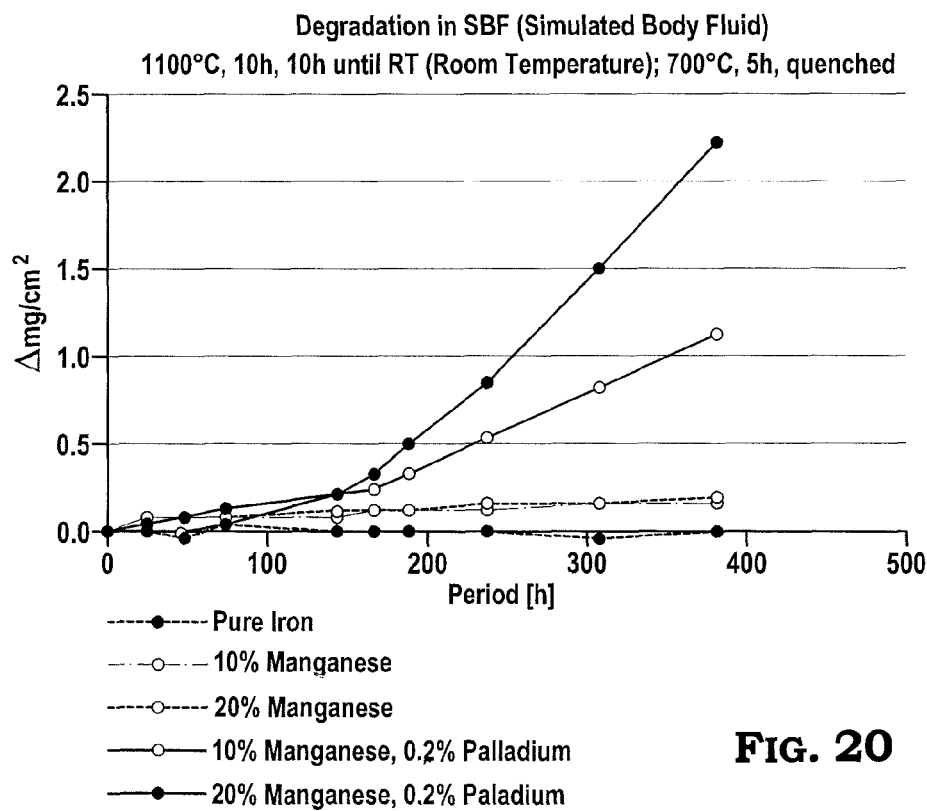
FIG. 20 is a graph of weight loss in SBF (1100° C./10 h/slowly+700° C./5 h)

FIG. 19 shows the weight loss in SBF (1100° C./10 h/H$_2$O+ 700° C./5 h). FIG. 20 shows the weight loss in SBF (1100° C./10 h/slow+700° C./5 h).

The results of the storage experiments in SBF are illustrated in FIGS. 19 and 20. It is noteworthy that all specimens containing manganese are degraded more rapidly than pure iron. The corrosion rate increases with an increase in Pd content. The type of heat treatment has a great influence on the respective degradation rates of the alloys. It is assumed that the results are determined by the segregation of elements. It has been confirmed by optical evaluation that crevice corrosion is dominant.

Iron alloys containing manganese thus have a significantly lower resistance to corrosion on the whole than pure iron. The manganese and palladium contents and the type of heat treatment influence the development of the structure (martensitic or austenitic), the physical properties (magnetic/nonmagnetic and/or Curie temperature) and the mechanical properties as well as the corrosion rate.

Tensile Test Data for the FeMn(10-20)Pd1 Alloy Series

The FeMn10Pd1, FeMn15Pd1 and FeMn20Pd1 alloys were produced according to the specifications given hereinabove. The initial state of the alloys was "solution-annealed," i.e., slow cooling in the furnace (approximately 100° C./h) from 850° C. was implemented.

In the starting state, the FeMn10Pd1 alloy is martensitic (alpha-martensite) and is thus ferromagnetic; the FeMn15Pd1 alloy has multiple phases (alpha-martensite, austenite and epsilon-martensite) and is therefore ferromagnetic; the FeMn20Pd1 alloy has two phases: austenitic+epsilon-martensitic and paramagnetic (very slightly ferromagnetic). Although epsilon-martensite is paramagnetic, Mn has a special very complex spin structure and is difficult to understand with respect to magnetic properties.

It has now surprisingly been found that a strain-induced phase transition occurs in the tensile test, and the ferromagnetic content increases significantly in FeMn15Pd1 and FeMn20Pd1. Thus, all exemplary embodiments in the deformed state are ferromagnetic, so this property (development of artifacts in imaging methods) can be utilized for monitoring degradation).

Figure 21:
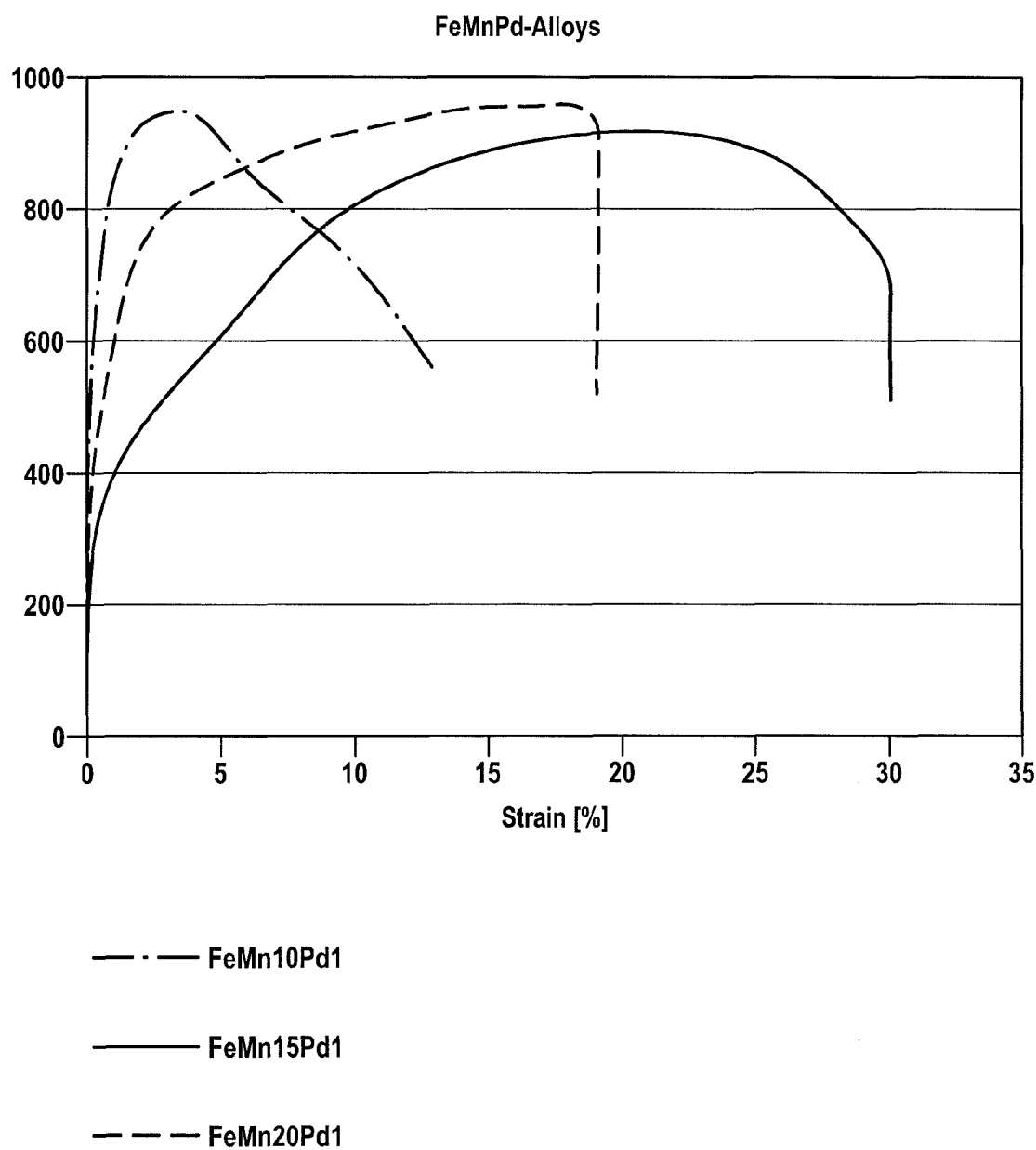
FIG. 21 is a graph of a tensile test on FeMnPd alloy.

The stress-strain curves show clearly the pronounced strain hardening (FIG. 21). In FeMn15Pd1 and FeMn20Pd1, we obtain values of more than 800 MPa at 15% strain (ballooning), which is a prerequisite for a highly filigree design of the stent (reduction in strut thickness). In the FeMn15Pd1 alloy, a yield point in the range of 350 MPa and a maximum strength (ultimate tensile strength) in the range of 900 MPa are found.

All patents, patent applications and publications referred to herein are incorporated by reference in their entirety.

What is claimed is:

1. An implant having a base body, the base body at least partially comprising:
at least one of the following:
(i) a biocorrodible iron alloy of formula (1):

Fe—P             (1)

where the amount of P in the alloy is from 0.05 to 5 wt %, and where the remainder of the alloy consists essentially of Fe plus impurities due to the production process; or (ii) a biocorrodible iron alloy of formula (2):

Fe—Mn—X             (2)

where the Mn content of the alloy is from 5 to 30 wt %, X is one or more elements selected from the group consisting of Pt, Pd, Ir, Rh, Re, Ru and Os, and the amount of X in the alloy is from 0 to 20 wt %, and where the remainder of the alloy consists essentially of Fe plus impurities due to the production process; or (iii) a biocorrodible iron alloy of formula (3):

Fe—Z             (3)

where Z is Pt, and the amount of Z in the alloy is from 5 to 30 wt %, and where the remainder of the alloy consists essentially of Fe plus impurities due to the production process.

2. The implant according to claim 1, wherein the iron alloy of formula (2) is present and wherein the amount of Mn in the iron alloy of formula (2) is from 10 to 27 wt %.

3. The implant according to claim 1, wherein the iron alloy of formula (2) is present, and wherein the amount of X in the iron alloy of formula (2) is from 0.01 to 10 wt %.

4. The implant according to claim 1, wherein the iron alloy of formula (2) is present, and wherein the iron alloy of formula (2) further consists essentially of either N or C in an amount of from 0 to 0.8 wt % of the iron alloy.

5. The implant according to claim 1, wherein the implant is either a stent, a clip or an occluder.

6. The implant according to claim 1, wherein the implant is designed for treatment of hyperthermia.

7. The implant according to claim 1 wherein the base body consists essentially of the biocorrodible iron alloy of formula 2.

8. The implant according to claim 7, wherein the amount of Mn is from 10 to 27 wt %.

9. The implant according to claim 7, wherein the amount of X is from 0.01 to 10 wt %.

10. The implant according to claim 7, wherein the amount of Mn is from 10 to 20 wt %, and wherein the amount of X is from 0.01 to 10 wt %.

11. The implant according to claim 7, wherein X is Pd.

12. The implant according to claim 7, wherein the iron alloy further consists essentially of either N or C in an amount of from 0 to 0.8 wt % of the iron alloy.

13. The implant according to claim 7, wherein the iron alloy has at least two phases in equilibrium.

14. The implant according to claim 13, wherein the two phases have different electrochemical properties.

15. The implant according to claim 1 wherein the base body consists essentially of the biocorrodible iron alloy of formula 3.

16. The implant according to claim 15, wherein the iron alloy has two phases in equilibrium.

17. The implant according to claim 16, wherein the two phases have different electrochemical properties.

18. An implant having a base body, the base body consisting essentially of at least one of the following:
a biocorrodible iron alloy of formula (1):

$$\text{Fe—P} \qquad (1)$$

where the amount of P in the alloy is from 0.01 to 5 wt %, and where the remainder of the alloy consists essentially of Fe plus impurities due to the production process; or (ii) a biocorrodible iron alloy of formula (2):

$$\text{Fe—Mn—X} \qquad (2)$$

where the Mn content of the alloy is from 5 to 30 wt %, X is one or more elements selected from the group consisting of Pt, Pd, Ir, Rh, Re, Ru and Os, and the amount of X in the alloy is from 0 to 20 wt %, and where the remainder of the alloy consists essentially of Fe plus impurities due to the production process; or (iii) a biocorrodible iron alloy of formula (3):

$$\text{Fe—Z} \qquad (3)$$

where Z is Pt, and the amount of Z in the alloy is from 5 to 30 wt %, and where the remainder of the alloy consists essentially of Fe plus impurities due to the production process.

19. An implant having a base body, the base body consisting essentially of:
a biocorrodible iron alloy of formula Fe—P where the amount of P in the alloy is from 0.01 to 5 wt %, and where the remainder of the alloy consists essentially of Fe plus impurities due to the production process.

* * * * *